US009421304B2

(12) United States Patent
Shortkroff et al.

(10) Patent No.: US 9,421,304 B2
(45) Date of Patent: *Aug. 23, 2016

(54) METHOD FOR IMPROVEMENT OF DIFFERENTIATION OF MESENCHYMAL STEM CELLS USING A DOUBLE-STRUCTURED TISSUE IMPLANT

(75) Inventors: Sonya Shortkroff, Braintree, MA (US); Joseph Khoury, Dedham, MA (US); Laurence J. B. Tarrant, Northampton, MA (US); Hans P. I. Claesson, Wayland, MA (US); Robert Lane Smith, Palo Alto, CA (US)

(73) Assignee: Histogenics Corporation, Waltham, MA (US)

( * ) Notice: Subject to any disclaimer, the term of this patent is extended or adjusted under 35 U.S.C. 154(b) by 335 days.

This patent is subject to a terminal disclaimer.

(21) Appl. No.: 12/195,255

(22) Filed: Aug. 20, 2008

(65) Prior Publication Data

US 2009/0069903 A1   Mar. 12, 2009
US 2016/0206787 A9   Jul. 21, 2016

Related U.S. Application Data

(63) Continuation-in-part of application No. 11/894,124, filed on Aug. 20, 2007.

(60) Provisional application No. 60/967,886, filed on Sep. 6, 2007, provisional application No. 60/958,401, filed on Jul. 3, 2007.

(51) Int. Cl.
*A61F 2/02* (2006.01)
*A61B 17/08* (2006.01)
(Continued)

(52) U.S. Cl.
CPC ............. *A61L 27/3839* (2013.01); *A61L 27/24* (2013.01); *A61L 27/3804* (2013.01); *A61L 27/56* (2013.01)

(58) Field of Classification Search
CPC ......... A61L 27/44; A61L 27/54; A61L 27/56; A61L 27/58
USPC ...................... 623/23.72, 16.11, 23.76, 11.11; 433/226; 424/426
See application file for complete search history.

(56) References Cited

U.S. PATENT DOCUMENTS 4,182,655 A   1/1980   Hartmeier
4,280,954 A   7/1981   Yannas et al.
(Continued)

FOREIGN PATENT DOCUMENTS

EP   1452191 A2   9/2004
EP   1923457 A1   5/2008
(Continued)

OTHER PUBLICATIONS

International Search Report and Written Opinion (PCT/US2008/007610) Oct. 8, 2008.
(Continued)

*Primary Examiner* — Todd J Scherbel
(74) *Attorney, Agent, or Firm* — Brown Rudnick LLP; Thomas C. Meyers

(57) ABSTRACT

A double-structured tissue implant (DSTI) and a method for preparation and use thereof for implantation into tissue defects. The double-structured tissue implant for differentiation, growth and transformation of cells, stem cells, mesenchymal stem cells and bone marrow stem cells. DSTI comprising a primary scaffold and a secondary scaffold consisting of a soluble collagen solution in combination with a non-ionic surfactant generated and positioned within the primary scaffold.

20 Claims, 17 Drawing Sheets

(51) Int. Cl.
*A61L 27/38* (2006.01)
*A61L 27/24* (2006.01)
*A61L 27/56* (2006.01)

(56) References Cited

U.S. PATENT DOCUMENTS

| | | | |
|---|---|---|---|
| 4,350,629 A | 9/1982 | Yannas et al. | |
| 4,448,718 A | 5/1984 | Yannas et al. | |
| 4,522,753 A | 6/1985 | Yannas et al. | |
| 4,851,354 A | 7/1989 | Winston et al. | |
| 4,912,032 A | 3/1990 | Hoffman et al. | |
| 5,116,824 A | 5/1992 | Miyata et al. | |
| 5,206,028 A | 4/1993 | Li | |
| 5,522,753 A | 6/1996 | McGraw | |
| 5,629,191 A * | 5/1997 | Cahn | 435/395 |
| 5,653,730 A * | 8/1997 | Hammerslag | 606/214 |
| 5,656,492 A | 8/1997 | Glowacki et al. | |
| 5,723,331 A | 3/1998 | Tubo et al. | |
| 5,759,190 A | 6/1998 | Vibe-Hansen et al. | |
| 5,786,217 A | 7/1998 | Tubo et al. | |
| 5,830,493 A * | 11/1998 | Yokota et al. | 424/426 |
| 5,876,444 A | 3/1999 | Lai | |
| 5,902,741 A | 5/1999 | Purchio et al. | |
| 5,928,945 A | 7/1999 | Seliktar et al. | |
| 5,972,385 A | 10/1999 | Liu et al. | |
| 5,989,269 A | 11/1999 | Vibe-Hansen et al. | |
| 6,042,610 A | 3/2000 | Li et al. | |
| 6,080,194 A | 6/2000 | Pachence et al. | |
| 6,103,255 A * | 8/2000 | Levene et al. | 424/426 |
| 6,150,163 A | 11/2000 | McPherson et al. | |
| 6,156,572 A | 12/2000 | Bellamkonda et al. | |
| 6,171,610 B1 | 1/2001 | Vacanti et al. | |
| 6,294,202 B1 | 9/2001 | Burns et al. | |
| 6,306,169 B1 * | 10/2001 | Lee et al. | 623/11.11 |
| 6,312,725 B1 | 11/2001 | Wallace et al. | |
| 6,322,563 B1 | 11/2001 | Cummings et al. | |
| 6,432,713 B2 | 8/2002 | Takagi et al. | |
| 6,447,701 B1 | 9/2002 | Heschel et al. | |
| 6,454,811 B1 | 9/2002 | Sherwood et al. | |
| 6,511,958 B1 | 1/2003 | Atkinson et al. | |
| 6,528,052 B1 | 3/2003 | Smith et al. | |
| 6,632,651 B1 | 10/2003 | Nevo et al. | |
| 6,652,872 B2 | 11/2003 | Nevo et al. | |
| 6,673,286 B2 | 1/2004 | Shih et al. | |
| 6,737,072 B1 | 5/2004 | Angele et al. | |
| 6,773,723 B1 | 8/2004 | Spiro et al. | |
| 6,790,454 B1 | 9/2004 | Malak et al. | |
| 6,875,442 B2 | 4/2005 | Holy et al. | |
| 6,893,466 B2 | 5/2005 | Trieu | |
| 6,896,904 B2 | 5/2005 | Spiro et al. | |
| 6,939,562 B2 * | 9/2005 | Spiro et al. | 424/488 |
| 6,949,252 B2 | 9/2005 | Mizuno et al. | |
| 6,989,034 B2 | 1/2006 | Hammer | |
| 6,991,652 B2 | 1/2006 | Burg | |
| 7,025,916 B2 | 4/2006 | Bachrach | |
| 7,148,209 B2 | 12/2006 | Hoemann et al. | |
| 7,208,177 B2 | 4/2007 | Geistlich et al. | |
| 7,309,232 B2 * | 12/2007 | Rutherford et al. | 433/226 |
| 7,537,780 B2 * | 5/2009 | Mizuno et al. | 424/423 |
| 7,560,432 B2 | 7/2009 | Kusanagi et al. | |
| 7,595,062 B2 * | 9/2009 | Pedrozo et al. | 424/422 |
| 8,030,361 B2 | 10/2011 | Aso et al. | |
| 8,070,827 B2 | 12/2011 | Shortkroff | |
| 8,685,107 B2 * | 4/2014 | Claesson et al. | 623/23.72 |
| 9,149,562 B2 | 10/2015 | Shortkroff et al. | |
| 2001/0021529 A1 | 9/2001 | Takagi | |
| 2001/0055615 A1 | 12/2001 | Wallace et al. | |
| 2002/0082220 A1 | 6/2002 | Hoemann et al. | |
| 2002/0082623 A1 | 6/2002 | Osther et al. | |
| 2002/0106625 A1 | 8/2002 | Hung et al. | |
| 2002/0115208 A1 | 8/2002 | Mitchell et al. | |
| 2003/0040113 A1 | 2/2003 | Mizuno et al. | |
| 2003/0095993 A1 | 5/2003 | Bentz et al. | |
| 2004/0197367 A1 * | 10/2004 | Rezania et al. | 424/422 |
| 2004/0197375 A1 * | 10/2004 | Rezania et al. | 424/426 |
| 2005/0038520 A1 * | 2/2005 | Binette et al. | 623/18.11 |
| 2005/0042254 A1 | 2/2005 | Freyman | |
| 2005/0186685 A1 * | 8/2005 | Kange et al. | 436/180 |
| 2005/0255458 A1 | 11/2005 | Polansky | |
| 2006/0105015 A1 | 5/2006 | Perla | |
| 2006/0204445 A1 | 9/2006 | Atala | |
| 2006/0286144 A1 * | 12/2006 | Yang et al. | 424/426 |
| 2007/0065943 A1 * | 3/2007 | Smith et al. | 435/395 |
| 2007/0178159 A1 * | 8/2007 | Chen et al. | 424/484 |
| 2007/0202190 A1 * | 8/2007 | Borden | 424/549 |
| 2007/0219497 A1 | 9/2007 | Johnson et al. | |
| 2008/0031923 A1 * | 2/2008 | Murray et al. | 424/426 |
| 2008/0260801 A1 * | 10/2008 | Ahlers et al. | 424/426 |
| 2009/0012628 A1 | 1/2009 | Shortkroff et al. | |
| 2009/0143867 A1 * | 6/2009 | Gage et al. | 623/23.72 |
| 2013/0273121 A1 | 10/2013 | Mizuno et al. | |

FOREIGN PATENT DOCUMENTS

| | | |
|---|---|---|
| FR | 2657352 A1 | 7/1991 |
| JP | 3-170693 | 7/1991 |
| JP | 622744 | 2/1994 |
| WO | 96/15818 A1 | 5/1996 |
| WO | 9844874 A1 | 10/1998 |
| WO | 00/31130 A1 | 6/2000 |
| WO | 0102030 A2 | 1/2001 |
| WO | 2005023321 A2 | 3/2005 |
| WO | 2007/035778 A2 | 3/2007 |
| WO | 2007/057175 A2 | 5/2007 |

OTHER PUBLICATIONS

Supplementary European Search Report for EP08768602.8 dated Oct. 22, 2012, 6 pages.

International Search Report for PCT/US2008/073762 dated Dec. 22, 2008, 3 pages.

International Preliminary Report on Patentability for PCT/US2008/073762 dated Feb. 24, 2010, 6 pages.

Supplementary European Search Report for EP08798300.3 dated Oct. 18, 2012, 6 pages.

R. Coulson, CML Clokie, S Peel: "Collagen and a thermally reversible poloxamer deliver demineralized bone matrix (DBM) and biologically active proteins to sites of bone regeneration" In: Portland Bone Symposium, Jeffrey O. Hollinger: "Proceedings from Portland Bone Symposium," Aug. 7, 1999, Oregon Health Sciences University, US, XP002685077, pp. 619-637.

Guoping Chen, et al., "Hybrid Biomaterials for Tissue Engineering: A Preparative Method for PLA or PLGA-Collagen Hybrid Sponges," Adv. Mater. 2000, 12, No. 6, pp. 455-457.

European Search Report and Opinion for EP11190811.7 dated Feb. 14, 2012, 10 pages.

International Preliminary Examination Report for PCT/US02/09001 dated Oct. 30, 2004, 7 pages.

International Search Report for PCT/US02/09001 dated Mar. 27, 2003, 2 pages.

Richard W. Farndale, et al., A Direct Spectrophotometric Microassay For Sulfated Glycosaminoglycans In Cartilage Cultures, Connective Tissue Research, 9:247-248 (1982).

Smith, R., et al., "In vitro stimulation of articular chondrocyte mRNA and extracellular matrix synthesis by hydrostatic pressure," Journal of Orthopaedic Research, John Wiley & Sons, Inc., Needham, MA, vol. 14, No. 1, Jan. 1, 1996, pp. 53-60, XP002961860 ISSN: 0736-0266.

Supplementary European Search Report for EP02753826 dated Jul. 17, 2009, 2 pages.

Abraham, 1986, Human basic fibroblast growth factor: nucleotide sequence and genomic organization, EMBO J 5 (10):2523-2528.

Fujisato, 1996, Effect of basic fibroblast growth factor on cartilage regeneration in chondrocyte-seeded collagen sponge scaffold, Biomaterials 17:155-162.

(56) References Cited

OTHER PUBLICATIONS

Venkataraman, 1999, Molecular characteristics of fibroblast growth factor—fibroblast growth factor receptor—heparin-like like glycosaminoglycan complex, PNAS 96:3658-3663.

Parkkinen, 1995, Influence of short-term hydrostatic pressure on organization of stress fibers in cultured chondrocytes, J Orth Res 13(5):495-502.

European Search Report and Opinion for EP11190811.7 dated Feb. 14, 2012, (10 pages).

International Preliminary Examination Report for PCT/US02/09001 dated Oct. 30, 2004, (7 pages).

International Search Report for PCT/US02/09001 dated Mar. 27, 2003, (2 pages).

Farndale et al., 1982, A Direct Spectrophotometry Microassay For Sulfated Glycosaminoglycans In Cartilage Cultures, Connective Tissue Research 9:247-248.

Smith et al., 1996, In vitro stimulation of articular chondrocyte mRNA and extracellular matrix synthesis by hydrostatic pressure, Journal of Orthopaedic Research 14(1):53-60.

Supplementary European Search Report for EP02753826 dated Jul. 17, 2009, (2 pages).

* cited by examiner

DSTI Implantation

DSTI Implantation With Microfracture

DSTI Implantation with Microfracture

Implantation of DSTI Seeded/Cultured with Cells/Bone Marrow

Preformed DSTI seeded with *in vitro* cultured cells

Prepare Defect Site
Trim DSTI to Fill Defect Site

Apply Adhesive to Defect Site

Place DSTI in Defect Site

Seal the Defect with Adhesive

DSTI implantation with Bone Marrow

Prepare Defect Site
Trim DSTI to Fill Defect Site

Rehydrate DSTI with Freshly
Aspirated Bone Marrow Undiluted
Or Diluted with Saline Place DSTI in Defect Site Seal the Defect with Adhesive

METHOD FOR IMPROVEMENT OF DIFFERENTIATION OF MESENCHYMAL STEM CELLS USING A DOUBLE-STRUCTURED TISSUE IMPLANT This application claims priority of the Provisional application Ser. No. 60/967,886, filed Sep. 6, 2007, and also is a continuation-in-part of the U.S. application Ser. No. 11/894,124 filed on Aug. 20, 2007, which application claims priority of the Provisional application Ser. No. 60/958,401, filed Jul. 3, 2007, the contents of each of which are incorporated by reference.

BACKGROUND OF THE INVENTION

Field of Invention

The current invention concerns a method for improvement of differentiation and transformation of cells, stem cells, mesenchymal stem cells, bone marrow mesenchymal cells and chondrocytes cultured in a double-structured tissue implant (DSTI) and a method for determination of a rate of differentiation, transformation or migration of such cells. The invention further concerns use of differentiated and transformed cells migrated and cultured in the DSTI for implantation into tissue defects.

In particular, the invention concerns a double-structured tissue implant (DSTI) comprising a primary scaffold and a secondary scaffold generated and positioned within the primary scaffold. The primary scaffold is a porous collagen-comprising material having randomly or non-randomly oriented pores of substantially homogeneous defined diameter. Under the most favorable conditions, the pores are vertically oriented and represent a high percentage of the porosity of the scaffold. The secondary scaffold is generated within the primary scaffold by introducing a composition comprising a soluble collagen solution in combination with a non-ionic surfactant into the pores of the primary scaffold and solidifying said composition within said pores using a process comprising lyophilization and dehydrothermal treatment.

Each, the primary and secondary scaffold, independently, or together, provides a structural support for cells and/or each separately may contain cells, progenitor cells, pharmaceutical agents or growth modulators.

The DSTI has improved stability, resistance to shrinkage, swelling, dissolution, wetting, storageability, an increased surface area for cell adhesion, growth, differentiation and/or transformation, chemotactic properties for cells or progenitor cells as well as properties conducive to cell differentiation and transformation.

The chemotactic propeties of DSTI toward mesenchymal stem cells and bone marrow stem cells are enhanced with addition of morphogenic growth factors that initiate gene expression of mesenchymal stem cell (MSC) and bone marrow mesenchymal stem cells (BMSC). Newly expressed mesenchymal stem cell and bone marrow mesenchymal stem cells cultured in the DSTI differentiate to the chondrocyte phenotype and ultimately into chondrocytes that are producing extracellular matrix leading to production of a new hyaline cartilage.

BACKGROUND AND RELATED DISCLOSURES

Articular (hyaline) cartilage is a highly organized avascular tissue composed of chondrocytes embedded within an extracellular matrix of collagens, proteoglycans, noncollagenous proteins and glycoproteins which make up about 20-40% of the wet weight of the tissue. The chemical bonding between the water and the matrix molecules provides for the smooth articulation of joint surfaces, and acts as a cushion in response to compressive, tensile and shearing forces. Because cartilage is avascular, it has little capacity for self-repair and untreated lesions will result in continued damage to the joint which eventually leads to osteoarthritis.

Current treatment options for osteoarthritis or articular cartilage injuries include microfracture, autologous chondrocyte implantation and osteochondral autograft or allograft transplantation (OATS). Each of these treatments has certain disadvantages. Microfracture leads to the development of fibrocartilage which is inferior to a hyaline cartilage because it lacks the biomechanical strength to support the compressive loads. Autologous chondrocyte implantation requires cartilage biopsy and, therefore, a second surgery, and is thus a technically challenging procedure. Osteochondral autograft transplantation has limitations as to host tissue availability for large lesions as well as limited availability of allograft material.

It would therefore be advantageous to have available a method and means to treat the injured or osteoarthritic cartilage that would be more practical and did not require multiple surgeries.

Collagen matrices for use as an implant for repair of cartilage defects and injuries are known in the art. Of a particular interest is a honeycomb structure developed by Koken Company, Ltd., Tokyo, Japan, under the trade name Honeycomb Sponge, described in the Japanese patent JP3170693, hereby incorporated by reference. Other patents related to the current subject disclose collagen-based substrates for tissue engineering (U.S. Pat. No. 6,790,454) collagen/polysaccharide bi-layer matrix (U.S. Pat. No. 6,773,723), collagen/polysaccharide bi-layer matrix (U.S. Pat. No. 6,896,904), matrix for tissue engineering formed of hyaluronic acid and hydrolyzed collagen (U.S. Pat. No. 6,737,072), method for making a porous matrix particle (U.S. Pat. No. 5,629,191) method for making porous biodegradable polymers (U.S. Pat. No. 6,673,286), process for growing tissue in a macroporous polymer scaffold (U.S. Pat. No. 6,875,442), method for preserving porosity in porous materials (U.S. Pat. No. 4,522,753), method for preparation of collagen-glycosaminoglycan composite materials (U.S. Pat. No. 4,448,718), procedures for preparing composite materials from collagen and glycosaminoglycan (U.S. Pat. No. 4,350,629) and a crosslinked collagen-mucopolysaccharide composite materials (U.S. Pat. No. 4,280,954).

However, many of the above disclosed structures have uncontrolled and unpredictable parameters such as an uneven and uncontrolled porosity, uneven density of pores, uneven sizes of the pores and random distribution of pores within the support matrix. Such uncontrolled parameters lead to an uneven distribution of cells and to uneven distribution of extracellular matrix produced by the cells because the actual usable pore structure represents only a small percentage of the total implant. Additionally, when introduced into tissue defects or cartilage lesions during the surgery, these structures are difficult to handle as they are unstable and do not have appropriate wetting properties in that they may shrink or swell and, therefore, are not easily manipulated by a surgeon.

For a tissue implant to be suitable for implantation, particularly for implantation into the cartilage lesion, the implant needs to be stable, easily manipulated, easily stored in sterile form and have a long shelf-life.

In order to provide a more uniform and sterically stable support structure for implantation into a tissue defect or cartilage lesion, inventors previously developed a collagen matrix having narrowly defined size and density of pores wherein the pores are uniformly distributed, mostly vertically oriented and non-randomly organized. This matrix is disclosed in the co-pending patent application Ser. No. 11/523,833, filed on Sep. 19, 2006, hereby incorporated by reference in its entirety. Additionally, the acellular matrix suitable to be used as the primary scaffold is described by inventors in the U.S. Pat. No. 7,217,294, on May 15, 2007, hereby incorporated in its entirety.

However, even with the above-described improvements, a solution to problems faced by the surgeon during surgery is still lacking. A practicality needed for routine use of the tissue implants, such as, for example, the articular cartilage implants by the orthopedic surgeons, where the implant needs to be readily available, manipulatable, wettable, stable, sterile and able to be rapidly prepared and used for implantation, is still not achieved. All the previously described and prepared matrices or scaffolds require multiple steps before they are fully implantable.

Thus, it would be advantageous to have available an implant that would be easily manufactured and packaged, would be stable for extended shelf-life, would be easily manipulatable and rapidly wettable upon introduction into the lesion, could provide a support for cell migration and seeding, for cell differentiation and transformation and that could have, additionally, pre-incorporated drug or modulator in at least one compartment of the implant.

The implant should also allow the surgeon to introduce a drug or modulator during the surgical procedure.

It would also be an advantage to provide an implant with an increased area of internal membranes which, while not interfering with cell migration and nutrient exchange, nevertheless, would provide a substrate favorable to cell adhesion, growth and migration as well as cell differentiation, transformation and formation of hyaline cartilage.

It is, therefore, a primary object of this invention to provide an implant that would have a double-structure comprising of a primary scaffold and a secondary scaffold compartments where each compartment of the implant can assume a different function, be incorporated with cells, different drugs or modulators and/or be selectively chosen for performing the different functions following the implantation.

The current invention provides such double-structured tissue implant and/or a method for use and fabrication thereof by providing the double-structured tissue implant (DSTI) comprising a first scaffold providing a sterically stable and biocompatible support structure, preferably made of Type I collagen, having defined pore sizes and density with said pores organized mostly vertically, and a second scaffold wherein said second scaffold is formed within said pores of said first scaffold. The double-structured scaffold of the invention is stable, resistant to shrinkage, swelling and dissolution, rapidly wettable, prepared in the sterile storageable form having a long-shelf life that can be easily manipulated and surgically implanted.

All patents, patent applications and publications cited herein are hereby incorporated by reference in their entirety.

SUMMARY

One aspect of the current invention is a method for improvement of differentiation and transformation of cells, stem cells, mesenchymal stem cells, bone marrow mesenchymal stem cells or chondrocytes by introducing and culturing such cells in a double-structured tissue implant (DSTI).

Another aspect of the current invention is a double-structured tissue implant, process for preparation thereof and a method for use thereof for differentiation and transformation of cells, stem cells, mesenchymal stem cells, bone marrow mesenchymal stem cells or chondrocytes.

Yet another aspect of the current invention is a DSTI comprising migrated and cultured cells, stem cells, mesenchymal stem cells, bone marrow mesenchymal stem cells or chondrocytes suitable for implantation into tissue defects.

Still another aspect of the current invention is a method for determination of a rate of differentiation and transformation of cells, stem cells, mesenchymal stem cells, bone marrow mesenchymal stem cells or chondrocytes.

Still yet another aspect of the current invention is a double-structured tissue implant having two distinct qualitatively different compartments wherein each of the compartments may be independently seeded with cells, stem cells, mesenchymal stem cells, bone marrow mesenchymal stem cells or chondrocytes or wherein one or both compartments of the implant may comprise a pharmaceutical agent or growth modulator.

Another aspect of the current invention is a process for preparation of a double-structured implant by providing a primary porous scaffold prepared from a biocompatible collagen material wherein said scaffold has a substantially homogenous defined porosity and uniformly distributed randomly and non-randomly organized pores of substantially the same size of defined diameter of about 300±100 µm, wherein said primary scaffold is brought in contact with a soluble collagen based solution comprising at least one non-ionic surfactant (Basic Solution), wherein such solution is introduced into said pores of said primary scaffold, stabilized therein by precipitation or gelling, dehydrated, lyophilized and dehydrothermally processed to form a distinctly structurally and functionally different second scaffold within said pores of said primary scaffold.

Still yet another aspect of the current invention is a DSTI having chemotactic properties toward stem cells, mesenchymal stem cells and bone marrow stem cells that make these cells migrate into such DSTI, differentiate and/or be transformed within the DSTI wherein such differentiation and transformation is enhanced with addition of morhogenetic growth factors.

Yet another aspect of the current invention is a method for determination of a rate of differentiation and transformation of stem cells, mesenchymal stem cells and bone marrow stem cells seeded within a DSTI.

Still yet another aspect of the current invention is a method for implantation of the DSTI containing mesenchymal stem cells, bone marrow stem cells or bone marrow slurry in a tissue defect.

BRIEF DESCRIPTION OF FIGURES

FIG. 12A is a schematic illustration of a method for implantation of DSTI into the tissue lesion or defect where the DSTI is rehydrated with non-differentiated or pre-differentiated stem cells or mesenchymal stem cells. The stem or mesenchymal stem cells are first dissolved in a physiologically acceptable solution and such solution is applied to the dehydrated DSTI previously trimmed to a size and shape of the defect. Rehydrated DSTI is implanted into the defect and sealed with an adhesive. FIG. 12B illustrates a method for implantation of the DSTI with microfracture of the subchondral plate. The subchondral plate is penetrated and the rehydrated DSTI is placed in the defect as in FIG. 12A. After sealing the defect containing rehydrated DSTI with the adhesive, the marrow components are able to enter the DSTI through the microfracture. FIG. 12C illustrates a method for implantation of DSTI with microfracture as seen in FIG. 12B except that the adhesive is also applied to the bottom of the lesion in between the microfracture penetrations. The FIG. 12D shows the implantation of the DSTI into the tissue lesion where the DSTI is rehydrated with mesenchymal stem cells. The DSTI rehydrated with MSC is then implanted and the defect is sealed with adhesive. FIG. 12E show implantation of the DSTI seeded with bone marrow stem cells that were cultured and optionally could also be activated by applying a hydrostatic/constant pressure regimen. The DSTI seeded with these cultured and/or activated cells is placed into the lesion or defect and the defect is sealed with adhesive placed over the implant. FIG. 12F illustrates implantation of the DSTI into the tissue defect where the DSTI is rehydrated with freshly aspirated bone marrow that is either undiluted or diluted with saline or another physiologically acceptable solution.

DEFINITIONS

Figure 1:
FIG. 1 shows a scanning electron microscopic view of a hydrated double-structured tissue implant (DSTI).

As used herein:

"Double-structured tissue implant" or "DSTI" means a tissue implant prepared according to a process of the invention wherein the primary scaffold is loaded with a Basic Solution thereby forming a composite that is subsequently subjected to precipitation, dehydration and lyophilization to obtain a Lyophilized Composite that is subsequently treated with dehydrothermal (DHT) treatment to result in a stable double-structured tissue implant.

"Primary scaffold" means a porous honeycomb, sponge, lattice or another structure made of collagen or collagen based material having randomly or non-randomly oriented pores of substantially homogenous defined diameter. Under the most favorable conditions, the pores are vertically oriented and represent a high percentage of the porosity of the scaffold.

"Secondary scaffold" means a collagen based structure prepared from a collagen or collagen-based compound in the presence of a non-ionic surfactant. The secondary scaffold is generated within the primary scaffold by introducing a composition comprising a soluble collagen solution in combination with a non-ionic surfactant (Basic Solution) into the pores of the primary scaffold and solidifying said composition within said pores using a novel process of the invention.

"Basic Solution" means a solution comprising a collagen in admixture with a surfactant, preferably PLURONIC®-Type surfactant, neutralized to the pH of about 7.4. Basic Solution is used for preparation of the secondary scaffold.

"Composite" means a primary scaffold loaded with a composition comprising a precipitated or gelled soluble collagen in combination with a non-ionic surfactant (Basic Solution). The composite is in a hydrated form because the Basic Solution is added in a fluid form as a gel, suspension or solution.

"Lyophilized composite" means the hydrated "Composite", as defined above, that is subsequently subjected to a freezing and lyophilization step.

"Collagen matrix" means a collagen support matrix that is not lyophilized or dehydrothermally treated.

"Surfactant" means a non-ionic or ionic surfactant polymer. Suitable surfactants, such as PLURONIC®-Type polymers or TRITON®-Type polymers, are non-ionic co-polymer surfactants consisting of polyethylene and polypropylene oxide blocks.

"TRITON®-Type surfactants are commercially available derivatized polyethylene oxides, such as for example, polyethylene oxide p-(1,1,3,3-tetramethylbutyl)-phenyl ether, known under its trade name as TRITON®-X100. Other TRITON®-Type surfactants that may be suitable for use in the instant invention are TRITON® X-15, TRITON® X-35, TRITON® X-45, TRITON® X-114 and TRITON® X-102. TRITON® surfactant are commercially available from, for example, Union Carbide, Inc. PLURONIC®-Type surfactants are commercially available block co-polymers of polyoxyethylene (PEO) and polyoxypropylene (PPO) having the following generic organization of polymeric blocks: PEO-PPO-PEO (Pluronic) or PPO-PEO-PPO (Pluronic R). Exemplary PLURONIC®-Type surfactants are PLURONIC® F68, PLURONIC® F127, PLURONIC® F108, PLURONIC® F98, PLURONIC® F88, PLURONIC® F87, PLURONIC® F77, PLURONIC® F68, PLURONIC® 17R8 and PLURONIC® 10R8.

"The porosity" means a pore size defined by the diameter of holes within the primary scaffold as well as density of the pore distribution as a function of cross-sectional area in millimeters. Porosity is defined as a total volume of pores relative to the implant.

"Substantially homogeneous" means at least 85-99% homogeneity. Preferable homogeneity is between 95% and 99%.

"Substantially homogeneous porosity" means that a pore size and diameter is within pore size range of about 200-300±100 µm, preferably 300±50 µm, in diameter.

"Wettability" means an ability to quickly absorb a fluid into the DSTI without changes in the size and shape of the implant.

"Shrinkage" means a volumetric reduction in surface area in all dimensions of a double-structured tissue implant.

"Swelling" means a volumetric increase of a surface area in all dimensions of a double-structured tissue implant.

"Dissolution" means the act of a solid matter being solubilized by a solvent.

"Rehydration" means the act of hydrating, wetting or rewetting a dehydrated composite, lyophilized composite, stand alone secondary scaffold or double-structured tissue implant.

"Shape-memory" means the capacity of the rehydrated DSTI to maintain its shape and size after deformation.

"Dehydrothermal treatment" means removing water at low pressure and at high temperature for cross-linking of polymers.

"Top surface" means an apical or synovial side of the matrix turned toward the joint.

"Bottom surface" means basal, closest to bone surface of the matrix.

"Chondrocytes" means the cells naturally residing in articular cartilage.

"Stem cells" or "SC" means the human body's master cells, with the ability to grow into any one of the body's more than 200 cell types. Stem cells are the cells that can differentiate into many different cell types when subjected to the right biochemical signals.

"Mesenchymal stem cells" or "MSC" means multipotent stem cells that can proliferate and differentiate into a variety of cells types. Cell types that MSC have been shown to differentiate into include osteoblasts, chondrocytes, myocytes or adipocytes. MSCs can encompass multipotent cells derived from bone marrow or from other non-marrow tissues, such as adult muscle side-population cells or the Wharton's jelly present in the umbilical cord. MSCs have a large capacity for self-renewal while maintaining their multipotence. However, the capacity of cells to proliferate and differentiate is known to decrease with the age of the donor, as well as the time in culture. Further, no unique surface markers have been identified for MSCs.

"Bone marrow" means the soft, fatty, vascular tissue that fills most bone cavities and is the source of red blood cells and many white blood cells.

"Bone marrow stem cells", "bone marrow mesenchymal stem cells" or "BMSC" means the most primitive cells in the bone marrow or bloodstream or umbilical cord cells that after entering the bloodstream travel to the bone marrow.

"Stromal cells" means a highly heterogenous cell population consisting of multiple cell Types with different potentials for proliferation and differentiation.

"Human articular chondrocytes" or "hAC" means chondrocytes isolated from human articular cartilage.

"S-GAG" means sulfated glycosaminoglycan.

"AGC1" means aggrecan.

"COL 1A1" means Type I collagen gene.

"COL 2A1" means Type II collagen gene.

"RGMA" means repulsive guidance molecule.

"SOX9" means the chondrogenic transcription factor.

"COMP" means cartilage oligomeric matrix protein.

"RT-PCR" means reverse transcription-polymerase chain reaction used for quantification of gene expression through detection of messenger RNA (mRNA) levels.

"Cell modulator" means a pharmaceutical agent, drug, growth factor, growth hormone, mediator, enzyme promoting cell incorporation, enzyme promoting cell proliferation, enzyme promoting cell division, a pharmaceutically acceptable excipient, additive or buffer.

DETAILED DESCRIPTION OF THE INVENTION

The current invention concerns a method for treatment tissue defects by using a novel double-structured tissue implant (DSTI) that has properties resulting in chemotactic chemoattraction of cells, stem cells, mesenchymal stem cells, bone marrow mesenchymal cells and chondrocytes and in improvement of their differentiation and transformation when these cells are cultured in said DSTI. The invention further concerns a method for determination of a rate of differentiation, transformation or migration of such cells. The invention additionally concerns use of differentiated and transformed cells migrated or seeded into and cultured in the DSTI for implantation into tissue defects ultimately leading to production of hyaline cartilage or another replacement tissue.

The DSTI has improved stability, resistance to shrinkage, swelling, dissolution, wetting, storageability, an increased surface area for cell adhesion, growth, differentiation and/or transformation, as well as chemotactic properties for cells or progenitor cells. The chemotactic properties of DSTI toward mesenchymal stem cells and bone marrow stem cells are advantageously enhanced with addition of morphogenetic growth factors that initiate gene expression of mesenchymal stem cell (MSC) and bone marrow mesenchymal stem cells (BMSC) and their differentiation to the chondrocyte phenotype and extracellular matrix production leading to and resulting in production of a new hyaline cartilage.

Finally, the invention is directed to a double-structured tissue implant suitable for implantation into a tissue lesion, and to the method for use of said implant in a clinical setting for repair of tissue lesions. The DSTI is particularly suitable for implantation into articular cartilage defects where it facilitates regeneration and formation of new hyaline cartilage. The secondary scaffold facilitates better cell attachment while at the same time maintaining a porous character of the DSTI. The DSTI may be advantageously hydrated before or during surgery with a physiologically acceptable solution optionally containing cells, stem cells, mesenchymal stem cells or bone marrow stem cells or bone marrow slurry. The double-structured implant has improved properties compared to a single structured implant and provides for variability in use.

A scanning electron micrograph of a rehydrated double-structured tissue implant (DSTI) is seen in FIG. 1. FIG. 1 is a cross-section of the DSTI showing the multiple flat feather-like surfaces spanning the pores as well as struts and flaps throughout and within the implant's pores. These surfaces generated by combination of the primary and secondary scaffold are responsible for improved cell attachment. The DSTI is produced by a process disclosed in Section III.

I. Double-Structured Tissue Implant

Double-structured tissue implant (DSTI) is a composite structure comprising a primary scaffold and a secondary scaffold generated and positioned within the primary scaffold. The primary scaffold is a porous collagen-comprising material having randomly or non-randomly, preferably vertically, oriented pores of substantially homogeneous defined diameter. The primary scaffold represents a high percentage of the DSTI. The secondary scaffold is generated within the primary scaffold by introducing a composition comprising a soluble collagen solution in combination with a non-ionic surfactant into the pores of the primary scaffold and solidifying said composition within said pores using a specific multi-step process described in Section III.

The DSTI thus comprises two separate compartments, namely the primary scaffold that provides a structural support for the secondary scaffold incorporated within the primary scaffold. Each, the primary and secondary scaffold independently, or together, provides a structural support for cells and/or each separately may contain cells, progenitor cells, pharmaceutical agents or growth modulators.

A. The Primary Scaffold

The primary scaffold is a collagen-based matrix prepared as a honeycomb, lattice, sponge or any other similar structure made of a biocompatible and/or biodegradable collagen containing material of defined density and porosity that is stable, pliable, storageable and, most importantly, highly porous.

Typically, the primary scaffold is prepared from compounds influencing fibrillar organization, such as collagen, collagen-containing composition or collagen containing a polymer. Representative compounds suitable for preparation of the primary scaffold are a Type I collagen, Type II collagen, Type III collagen, Type IV collagen, Type VI collagen, gelatin, collagen containing agarose, collagen containing hyaluronan, collagen containing proteoglycan, collagen containing glycosaminoglycan, collagen containing glycoprotein, collagen containing glucosamine, collagen containing galactosamine, collagen containing fibronectin, collagen containing laminin, collagen containing growth factor, collagen containing cytokine, collagen containing elastin, collagen containing fibrin, collagen containing polylactic acid, collagen containing polyglycolic acid, collagen containing polyamino acid, collagen containing polycaprolactone, collagen containing polypeptide, a copolymer thereof, each alone or in combination. Additionally, the primary scaffold may be prepared from the collagen precursors such as, for example, peptide monomers, such as alpha 1 (Type I), and alpha 2 (Type I) collagen peptide or alpha 1 (Type I) alpha 2 (Type I) peptides, alone or in combination, or from a combination of precursors, such as 2 (alpha 1, Type I) peptide and 1 (alpha 2, Type I) peptide together with collagens, such as Type IX or Type XI collagen.

The collagen containing material used for preparation of the primary scaffold may further be supplemented with other compounds, such as pharmaceutically acceptable excipients, surfactants, buffers, additives and other biocompatible components.

Preferably, the primary scaffold of the invention is prepared from collagen and most preferably from Type I collagen or from a composition containing Type I collagen.

In one embodiment, the primary scaffold is a structure containing a plurality of narrowly defined randomly or non-randomly organized pores having a substantially homogeneous narrowly defined size and diameter that are uniformly distributed through the scaffold, dividing the scaffold space into columns or pore network. The exemplary primary scaffold is described in the co-pending application Ser. No. 11/523,833, filed on Sep. 19, 2006, herein incorporated by reference in its entirety.

In another embodiment, the primary scaffold may be the Type I collagen-based support matrix that is a porous honeycomb, sponge, lattice or scaffold having randomly or non-randomly organized pores of variable pore diameters such as described in, for example, the U.S. Pat. No. 7,217,294 on May 15, 2007, herein incorporated by reference.

In yet another embodiment the primary scaffold is a honeycomb collagen matrix developed by Koken Company, Ltd., Tokyo, Japan, under the trade name Honeycomb Sponge, described in the Japanese patent JP3170693, hereby incorporated by reference.

The primary scaffold according to the invention has, preferably, a substantially defined pore size in diameter and pore density in randomly or non-randomly organized manner that creates an apical (top) or basal (bottom) surface to the implant where the sizes and diameters of the pores on both the apical or basal surface are substantially the same. When used as a primary scaffold only, the scaffold provides conditions for a sterically-enhanced enablement of cells. Chondrocytes seeded in the primary scaffold, for example, have been shown to produce within said implant an extracellular matrix comprising glycosaminoglycan and Type II collagen in ratios characteristic for a normal healthy articular hyaline cartilage.

A secondary scaffold structure is generated within the pores of the primary scaffold. To that end, the primary scaffold is loaded with a composition suitable for preparation of the secondary scaffold (Basic Solution). Such composition comprises a soluble collagen, collagen-containing or collagen-like mixture, typically of Type I collagen, in combination with a non-ionic surfactant.

B. The Secondary Scaffold

The secondary scaffold is created or generated within the pores of the primary scaffold. The secondary scaffold is a qualitatively different structure formed within the confines of the first scaffold.

The secondary scaffold is generated by a process comprising preparing a soluble collagen-based composition as described below, further comprising a suitable non-ionic or ionic surfactant (Basic Solution).

The secondary scaffold comprises a collagen, methylated collagen, gelatin or methylated gelatin, collagen-containing and collagen-like mixtures, said collagen being typically of Type I or Type II, each alone, in admixture, or in combination, and further in combination with a surfactant, preferably a non-ionic surfactant. The suitable non-ionic surfactant is preferably a polymeric compound such as a PLURONIC®-Type polymer.

In preparation of the DSTI, said composition suitable for generation of the secondary scaffold within the primary scaffold is then brought into contact with a primary scaffold structure by absorbing, wicking, soaking or by using a pressure, vacuum, pumping or electrophoresis, etc., to introduce said composition for the secondary scaffold into the pores of the primary scaffold. In alternative, the primary scaffold may be immersed into the composition for the secondary scaffold. The primary scaffold containing basic solution is then processed according to Section III.

C. Surfactants

Improved properties of the DSTI, such as its rapid wettability and resistance to shrinkage, swelling and dissolution, are due to a presence of a secondary scaffold as a distinct functional entity.

The secondary scaffold prepared according to the process of the invention requires, as an essential part, a presence of a surfactant, preferably a non-ionic or, in some instances, even an ionic surfactant. The surfactant, preferably the non-ionic surfactant of Type such as TRITON® or PLURONIC®, preferably PLURONIC® F127, is an essential component of a composition used for preparation of the secondary scaffold, or micellar substrate bound to the implant. The presence of the surfactant improves stability and particularly wettability and rehydration properties of the implant without causing its shrinkage or swelling.

Suitable surfactants, such as PLURONIC®-Type polymers or TRITON®-Type polymers, are non-ionic co-polymer surfactants consisting of polyethylene and polypropylene oxide blocks.

TRITON®-Type surfactants are commercially available derivatized polyethylene oxides, such as for example, polyethylene oxide p-(1,1,3,3-tetramethylbutyl)-phenyl ether, known under its trade name as TRITON®-X100. Other TRITON®-Type surfactants that may be suitable for use in the instant invention are TRITON® X-15, TRITON® X-35, TRITON® X-45, TRITON® X-114 and TRITON® X-102. TRITON® surfactant are commercially available from, for example, Union Carbide, Inc.

PLURONIC®-Type surfactants are commercially available block co-polymers of polyoxyethylene (PEO) and polyoxypropylene (PPO) having the following generic organization of polymeric blocks: PEO-PPO-PEO (Pluronic) or PPO-PEO-PPO (Pluronic R). Exemplary PLURONIC®-Type surfactants are PLURONIC® F68, PLURONIC® F127, PLURONIC® F108, PLURONIC® F98, PLURONIC® F88, PLURONIC® F87, PLURONIC® F77, PLURONIC® F68, PLURONIC® 17R8 and PLURONIC® 10R8.

The most preferred non-ionic surfactant of PLURONIC®-Type suitable for use in the invention is a block co-polymer of polyoxyethylene (PEO) and polyoxypropylene (PPO) with two 96-unit hydrophilic PEO blocks surrounding one 69-unit hydrophobic PPO block, known under its trade name as PLURONIC® F127. PLURONIC® surfactants are commercially available from BASF Corp.

D. Double-Structured Tissue Implant

The double structured tissue implant (DSTI) is prepared by treating the primary scaffold loaded with a combination of the soluble collagen and non-ionic surfactant and processes according to the process for preparation of the DSTI described below in Section III, Scheme 1.

Briefly, the primary scaffold is loaded with the collagen/surfactant combination, precipitated or gelled, washed, lyophilized and dehydrothermally treated to solidify and stabilize the secondary scaffold within the pores of the primary scaffold.

The double-structured tissue implant can be seeded with cells, loaded with pharmaceutical agents, drugs or growth modulators. Additionally and preferably, the two of its distinct compartments, namely the primary scaffold and the secondary scaffold, can each be independently loaded with living cells, cell suspension, with a pharmaceutically effective agent or agents or with a growth modulator. These may be loaded into the implant individually or in any possible combination, such as, for example, where the cells may be introduced into one component and the drug into the second component, or the drug into one component and the modulator into the second component and/or any variation thereof.

Figure 2:
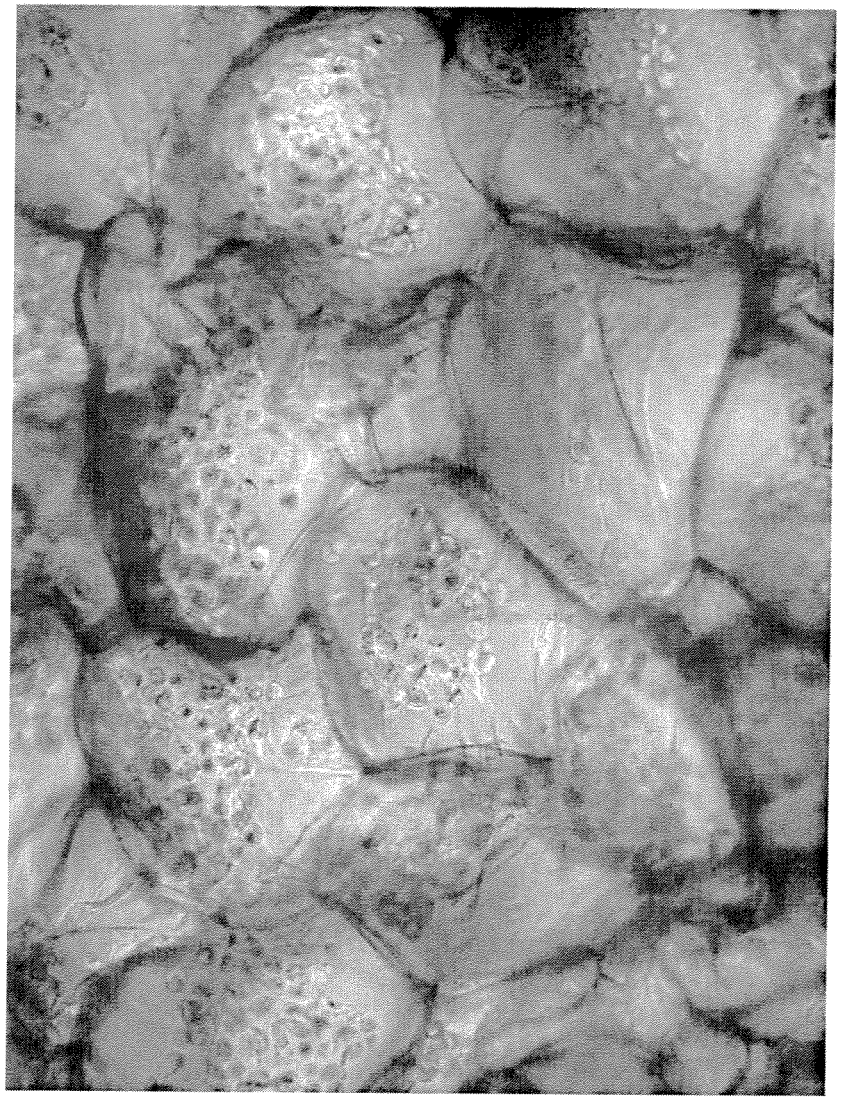
FIG. 2 is a photomicrograph of a DSTI showing pores filled with human chondrocytes.

The DSTI loaded with chondrocytes is shown in FIG. 2 wherein chondrocytes are seen to form clusters within the pores of the DSTI and retain their rounded morphology. The cells are seen to be well distributed within the pores of the DSTI and attached to the core (primary) scaffold or to the flaps and struts of the secondary scaffold.

The DSTI provides a biocompatible environment for culturing, growth, proliferation, differentiation and transformation of cell, particularly chondrocytes, stem cells, mesenchymal stem cells, bone marrow cells and bone marrow mesenchymal cells.

II. Properties of the Double-Structured Tissue Implant

The DSTI of the invention has distinctly improved properties when compared to the primary scaffold alone or to a composite loaded with a composition for preparation of the secondary scaffold (Composite), unprocessed, or to the Composite that has been frozen and lyophilized (Lyophilized Composite) but not dehydrothermally treated.

Typically, a tissue implant is implanted into a tissue defect during a surgery. Also typically, such surgery has a time-limit on implantation that has preferably about one hour window when the implant is placed into the defect. For these reasons, it is important that a specification for an implantable double-structured tissue implant provides stability, resistance to change in shape, size and shrinkage or swelling, resistance to dissolution, consistency with respect to pore size permitting an ingrowth of cells from the native tissue into the implant and conditions for synthesis and formation of extracellular matrix within the implant. The DSTI appears to have all the above properties.

Furthermore, the presence of the secondary scaffold improves the function of the DSTI by providing a multitude of small membranous attachment sites which can provide cell anchorage and phenotype stability while preserving the through porosity of the overall implant, thereby allowing nutrients and growth factors and migratory cells to permeate the implant.

A Stability of the Double-Structured Tissue Implant

From the point of view of the implantability, stability of the implant is one of the major requirements. The implant stability depends on several factors. There must be low or, preferably, no initial dissolution of collagen from the implant into the physiological fluids and there must be low or preferably no change in size and shape of the implant following rehydration or wetting before, during or after surgery prior to biodegradation in situ.

1. Collagen Retention and Resistance to Dissolution

One of the most important requirements for the implant is its resistance to dissolution of its components upon wetting and rehydration of said implant during implantation, during preparation of the implant for implantation and subsequently also after implantation. A minimally low dissolution or, preferably, no dissolution of the collagen component from the implant into the physiologic solution immediately after or before placement of the implant into the tissue defect and into an interstitial fluid, plasma or blood following the surgery, under normal physiological conditions ensures continued functionality of the implant following its implantation into the tissue defect, such as, for example into the cartilage lesion. Low or minimal dissolution of collagen from the implant means that the DSTI has the high retention of the collagen within the implant during the initial, most important implantation period.

In order to determine the stability of the implant subjected to transport and handling, an additional study was performed with and without agitation and the dissolution of collagen from the DSTI. These conditions were compared to the dissolution of collagen from the non-lyophilized composite (Composite). Results are not shown. These studies confirmed that even with agitation, there is a relatively small change in the accumulated release of collagen into the solution over a period of eight days but particularly during the first hour following the rehydration.

The DSTI has been shown to have almost complete retention of collagen and high resistance to dissolution during the implantation and immediately after implantation.

2. Resistance to Change in Size and Shape

Another important feature of the DSTI is its shape-memory, that is its resistance to change in size and shape. This feature is very important for implant efficacy as any change in the size and shape by shrinking or swelling can negatively effect the outcome of the implantation surgery. An implant that would get smaller by shrinking will not fill the defect, will not provide a structural support for migration of cells from the surrounding tissue or cell integration into the surrounding tissue and may also be dislodged from the defect. Swelling of the implant could, on the other hand, cause the implant to swell within the defect, decrease the structural support for cells and be rejected or ejected from the defect because of its larger size.

The resistance to change in shape and size means that for implantation into a defect of discernable size, the functional construct must not swell or shrink extensively upon rehydration during time of preparation before surgery or after placement of the implant into the defect.

The DSTI has been shown to have a high resistance to change in size and shape of the implant consistent with shape memory after hydration.

B. Viability of Cells Cultured in DSTI

Another important feature of the tissue implant is to provide support and conditions for cell migration from surrounding tissue into the implant or for the cell integration into surrounding tissue in a case when the cells are seeded into the DSTI before implanting. This feature is determined by cell viability within the DSTI and provides another criteria for determining functionality and usefulness of the DSTI.

In order for an implant to be functionally viable, the implant must provide a structural support for cells as well as provide or permit conditions to be provided for cell seeding into the implant, cell growth within the implant and/or cell migration into or from the surrounding tissue.

Conditions for cell seeding, their growth within the implant, their nutritional and metabolic needs are designed based on the type of cells that the implant is supposed to deliver and support. For example, if the implant is designed for repair of a skin defect, the cells and their requirement will be different than if the implant is designed for repair of a chondral or bone lesion. Conditions for structural support and conditions for promotion of cell growth, their migration and/or integration into the surrounding tissue will be adjusted based on the tissue where the DSTI will be implanted and the function the implant will assume in repair of the tissue defect.

While the DSTI of the invention is preferably suitable for use in treatment and repair of chondral, subchondral or bone lesions, the DSTI, as such, is suitable to be used for repair of any other tissue or tissue defect.

The successful implant, such as, for example, DSTI implanted into the cartilage lesion, must provide conditions allowing cells to form, generate and/or synthesize a new extracellular matrix (ECM). In this regard, the implant porous structure must allow cells to migrate, be attached or aggregate into and within the pores and function similarly to their normal function in the healthy tissue.

Consequently, the pore size of the implant and the consistency with respect to pore size for the ingrowth of cells is important both for cell adhesion, extracellular matrix production and cell to cell contact and communication. Depending on the tissue to be repaired, the pore size of the primary and/or secondary scaffold will vary. For example, cartilage scaffolds would have an optimal pore size of between 200-300±100 μm and bone would have a pore size in the range of 300 to 350±100 μm.

A significant advantage of having a double-structured tissue scaffold arises from the increase in mechanical integrity relative to a primary porous collagenous material because the polymerization creates fiber-like structure between the primary and secondary scaffold that serves as a reinforcing network for cells.

In addition, due to inclusion of the secondary scaffold there is an increase in overall surface area within the DSTI that permits cells spreading and migration throughout the interstices of the DSTI. At the same time, the secondary scaffold must be designed such that it is not of such high density that it becomes a blocking agent that acts as a steric hindrance for cell ingrowth and tissue repair.

DSTIs according to the invention have all the above properties.

Chondrocytes seeded in the DSTI are viable and proliferate as evidenced from testing for viability. Viability testing was performed as described in Example 5. In this study, the total number of cells and the percent of live cells that were retained in the DSTIs (DSTI-1-DSTI-3) over the course of 21 days in culture were determined. Results are seen in Table 1.

TABLE 1

| Percent Viability of Chondrocytes Seeded in DSTI | | |
|---|---|---|
| Group | Initial | 21 Days |
| DSTI-1 | 98 ± 1% | 97 ± 2% |
| DSTI-2 | 97 ± 2% | 100 ± 1% |
| DSTI-3 | 97 ± 2% I | 98 ± 1% |

Results summarized in Table 1 demonstrate that all three DSTIs had initially at least 97% viability and such viablity has not significantly changed after 3 weeks of culturing the DSTI seeded with chondrocytes.

Chondrocytes maintained the chondrocyte cartilage phenotype. Testing for chondrocyte phenotype included measurement of synthesis of chondrocyte specific extracellular matrix, namely production of S-GAG/DNA, by chondrocytes seeded in DSTIs. The testing was performed according to Example 6. An increase in S-GAG/DNA levels over time indicated that the environment is conducive to chondrocyte synthesis and deposition of ECM. Results are seen in FIG. 3.

Figure 3:
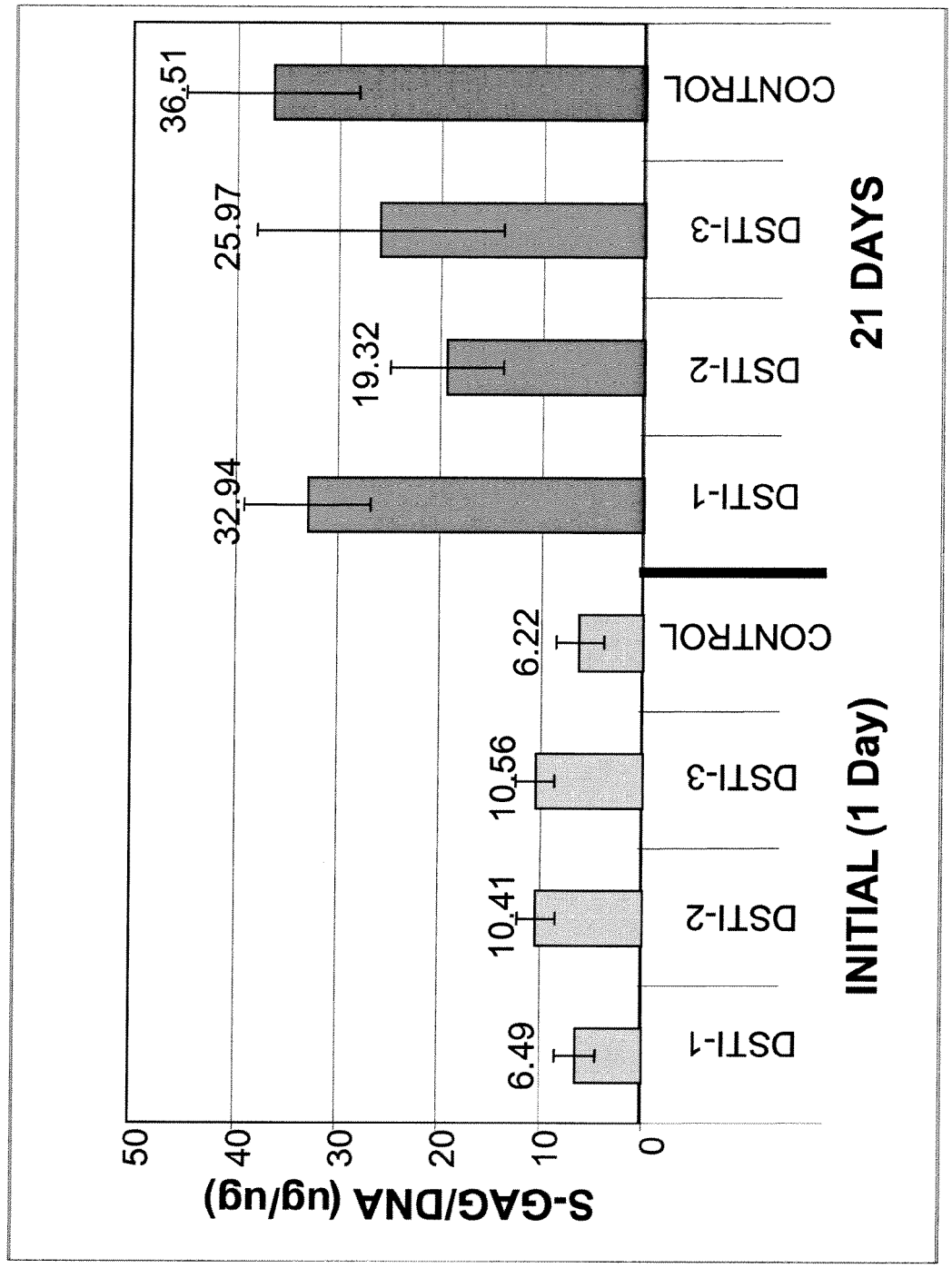
FIG. 3 is a graph illustrating compatibility of cells with DSTIs by determining production and accumulation of S-GAG/DNA in 21 days by chondrocytes embedded in DSTIs (DSTI-1-DSTI-3) and in a collagen matrix (control) that is not lyophilized or treated dehydrothermally.

In the study illustrated in FIG. 3, three DSTI discs and one collagen matrix that is not lyophilized and dehydrothermally treated (Control), seeded with chondrocytes were tested and compared initially and after 21 days in culture for production of S-GAG/DNA (μg/μg).

As seen in FIG. 3, all three DSTIs had significantly, between 2 and 5 fold, increased S-GAG deposition after 21 days in culture, when compared to the initial 24 hours reading. The levels of two of three DSTIs were not significantly different from the levels seen in non-treated collagen matrix used as a positive control, leading to the conclusion that seeding the cells within DSTI did not alter cell viability.

Chondrocytes seeded in the DSTI remained viable, proliferated and synthesized proteoglycan, as determined by increased synthesis of S-GAG. Proteoglycan is an extracellular matrix (ECM) constituent of cartilage. Moreover, over time, the S-GAG accumulated within the DSTIs indicating deposition of the ECM within DSTI. Results obtained in this study show that the DSTI provides a biocompatible environment for chondrocytes and other cells.

C. Chemotactic Properties of DSTI toward Chondrocytes MSC and BMSC

DSTI have been found to have chemoattraction for cells in general and particularly for MSC and BMSC. These cells were found to migrate into the DSTI. Such migration was proven to be important for treatment of tissue defects.

When DSTI is implanted into the tissue defect, its chemotactic properties attract and/or increase migration of stem cells and particularly bone marrow stem cells into the DSTI where they differentiate and/or are transformed into the appropriate differentiated cells that will begin to synthesize the extracellular matrix ultimately generating the hyaline cartilage or another target tissue.

D. Migration

The ability of multipotent, undifferentiated bone marrow stem cells to migrate toward and enter into the DSTI, to attach, grow, and differentiate into chondrocytes was studied using a procedure according to Example 7.

Following two or four weeks of culturing of DSTIs seeded with BMSC, individual DSTIs were removed and analyzed for DNA and S-GAG content. RT-PCR was used for determination of RNA expression of Type I collagen (COL 1A1), Type II collagen (COL 2A1), and aggrecan (AGC1).

Quantification of DNA within a cell-seeded DSTI showed that in a chondrogenic medium hAC proliferation was increased 2.6 fold and bone marrow stem cells fproliferation increased 1.5 fold when compared to non-chondrogenic medium.

Measurement of S-GAG levels showed that in chondrogenic medium hAC produced 3.1 fold more S-GAG and bone marrow stem cells produced 1.6 fold more S-GAG compared to non-chondrogenic medium. On a per cell basis, the bone marrow stem cells produced more S-GAG per amount of DNA, consistent with being metabolically active.

The DSTI was both supporting proliferation and ECM production in a different culture medium without showing negative effects on differentiation.

E. Gene Expression

Cells migrated into the DSTI show increased gene expression for collagen Type I, collagen Type II and aggrecan.

Human articular chondrocytes (hAC) in the DSTI exhibit an increase in Type I collagen and a decrease in Type II collagen and aggrecan production at 2 and 4 weeks. Such increase is possibly associated with the chondrocyte proliferation in chondrogenic medium. Results are seen in FIG. 4.

Figure 4:
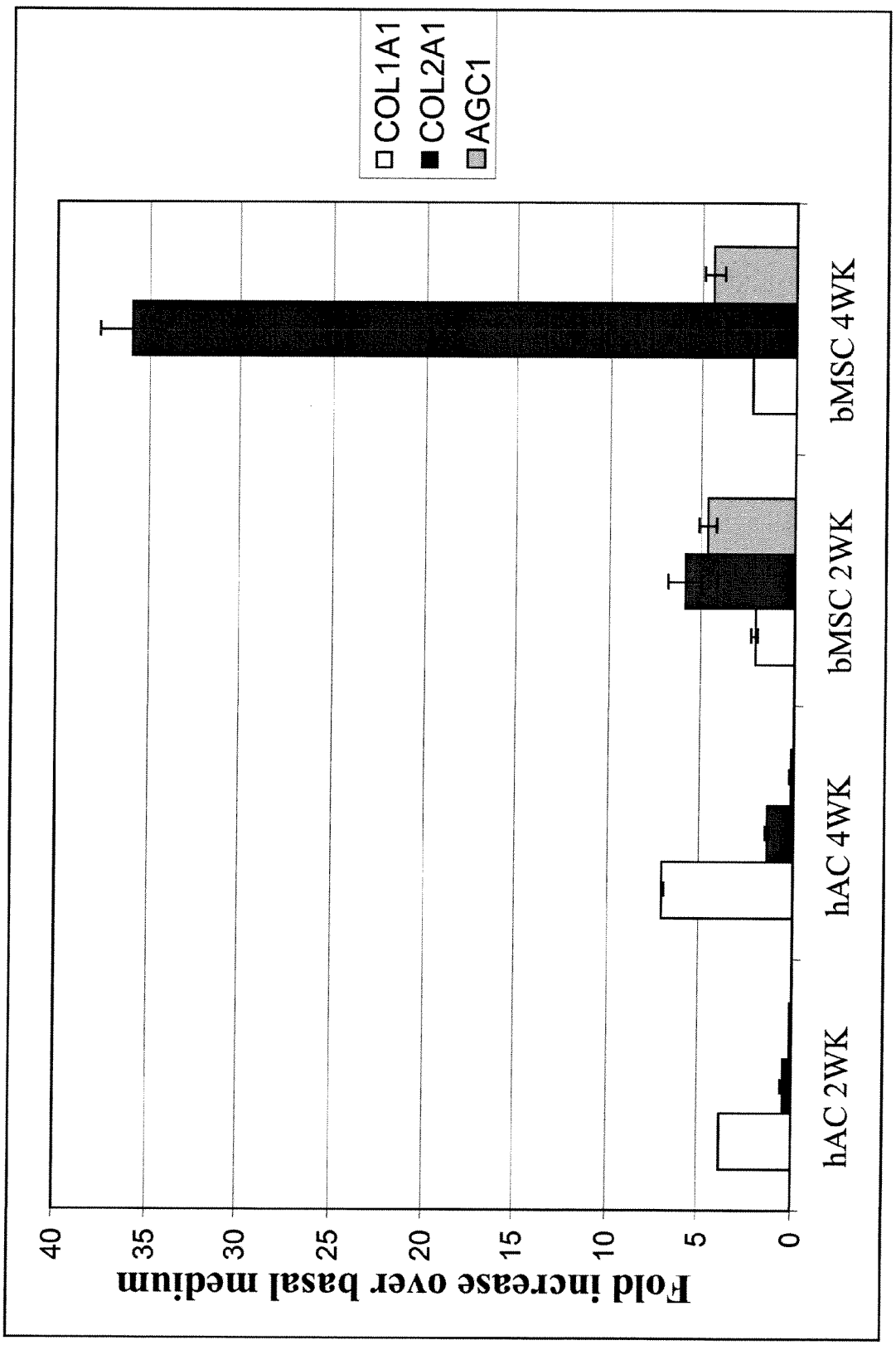
FIG. 4 is a graph showing gene expression of Type I collagen (COL 1A1), Type II collagen (COL 2A1) and aggrecan (AGC1) by bone marrow stem cells (BMSC) and by human articular chondrocytes (hAC) seeded in the DSTI and cultured for two (2 WK) and four weeks (4 WK).

FIG. 4 shows gene expression of Type II collagen by bone marrow stem cells in DSTI. Such expression is greatly increased after two and four weeks in culture. Specifically, FIG. 4 shows results of RT-PCR of bone marrow stem cells (BMSC). RT-PCR shows bone marrow stem cells differentiating into chondrogenic phenotype: collagen Type I (COL 1A1), collagen Type II (COL 2A1) and aggrecan (AGC1). For bone marrow stem cell, there was substantial increase in production of Type II collagen at four weeks of culture compared to the amount seen at two weeks of culture.

Results seen in FIG. 4 clearly show that bone marrow stem cells seeded in DSTI and grown in chondrogenic medium produce glycosaminoglycans and display differentiation markers indicative of the chondrocyte phenotype. By 4 weeks in culture, Type II collagen gene expression in the stem cell seeded in DSTI is dramatically up-regulated and the bone marrow stem cells are producing more S-GAG/cell than the articular chondrocytes.

The above studies clearly indicate that the DSTI supports gene expression of migrated cells and also that the culture medium has an important function in differentiation and migration of cells into DSTI.

The ability of human articular chondrocytes, bone marrow stem cells or bone marrow cells to migrate into DSTI and differentiate into chondrocytes was studied by migration assays using Boyden chambers, commonly used test to study the chemotaxis potential of a media/agent and migration ability of the cells. This study simulated the ability of bone marrow stem cells to migrate into a defect following microfracture surgery.

Evaluation of the study using the Boyden chamber assay, as described in Example 8, showed that human articular chondrocytes that migrated into DSTI remained in the DSTI. In general, a DNA content of cells substantiated a 4 fold increase in cell number in human articular chondrocytes that migrated into the DSTI as compared to those that were seeded in the DSTI as controls.

F. Production of Extracellular Matrix

Production of extracellular matrix by the individual cells is measured by the ratio of S-GAG to DNA. To determine the amount of extracellular matrix produced either by human articular chondrocytes or by bone marrow stem cells, another study was performed. Results of this study are shown in FIG. 5.

Figure 5:
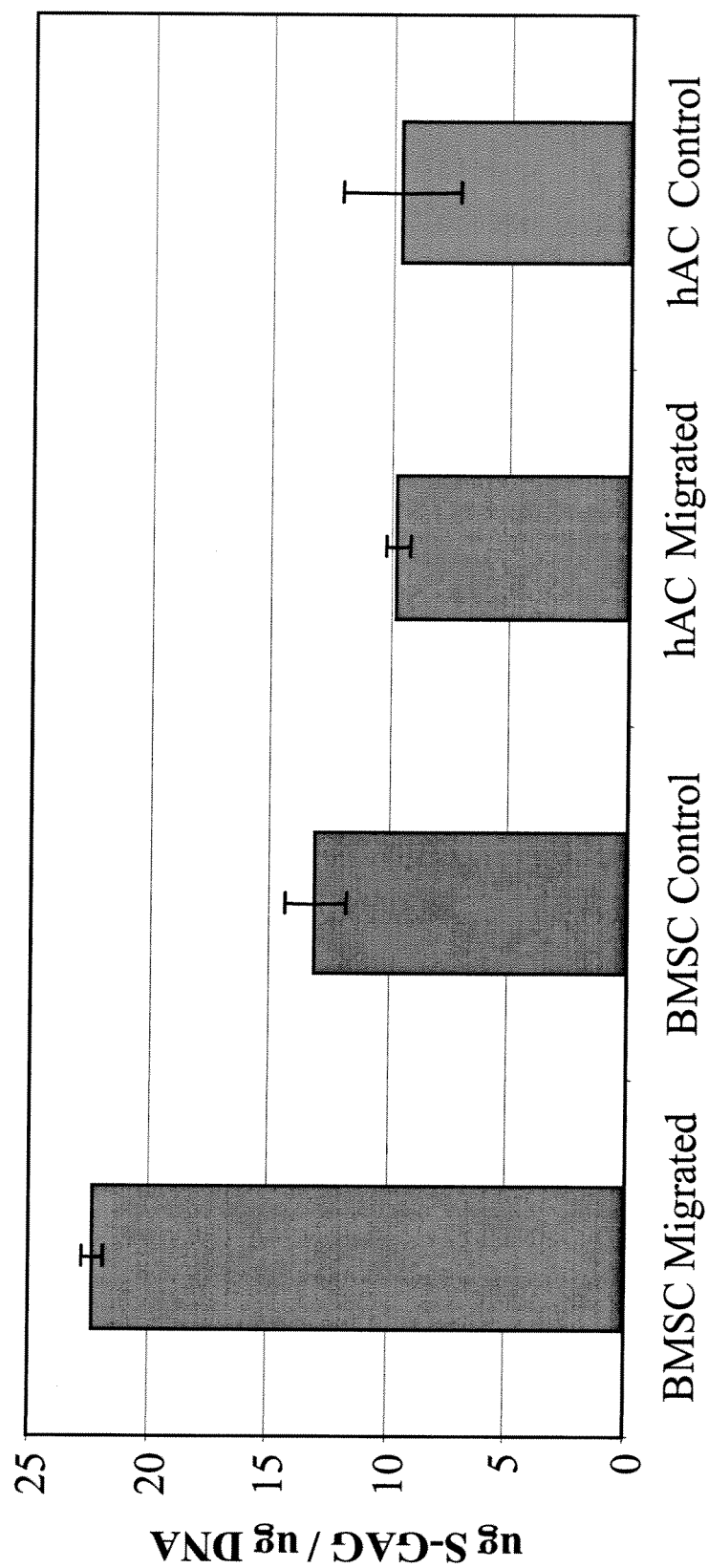
FIG. 5 is a graph illustrating migration of bone marrow stem cells (BMSC migrated) and human articular chondrocytes (hAC migrated) into the DSTI and production of S-GAG/DNA by these cells after four weeks of culture compared to BMSC and hAC controls without the DSTI.

FIG. 5 shows production of S-GAG/DNA by bone marrow stem cells (MSC) and human articular chondrocytes (hAC) after four weeks in culture. The cells were either placed in a Boyden chamber and allowed to migrate into the DSTI (Migrated) or were seeded directly into the DSTI (Control). As seen in FIG. 5, the bone marrow stem cells that migrated into the DSTI (MSC Migrated) produced almost twice as much S-GAG per cell than MSC seeded in the DSTI (MSC Control) and almost two and a half times more than human articular chondrocytes that either migrated into DSTI or were seeded in the DSTI. There was no observable difference between the amount of S-GAG production by human articular chondrocyte between the migrated cells into the DSTI and seeded cells in the DSTI.

The above results clearly show that the combination of DSTI with bone marrow stem cells cultured in an appropriate medium leads to increased differentiation of cells and increased production of extracellular matrix by the cells migrated into the DSTI.

Uniqueness of stem cells and particularly bone marrow stem cells behavior during migration into the DSTI is shown in another study where the gene expression of bone marrow stem cells migrating into the DSTI was determined vis-a-vis human articular chondrocytes. Results are seen in FIG. 6.

Figure 6:
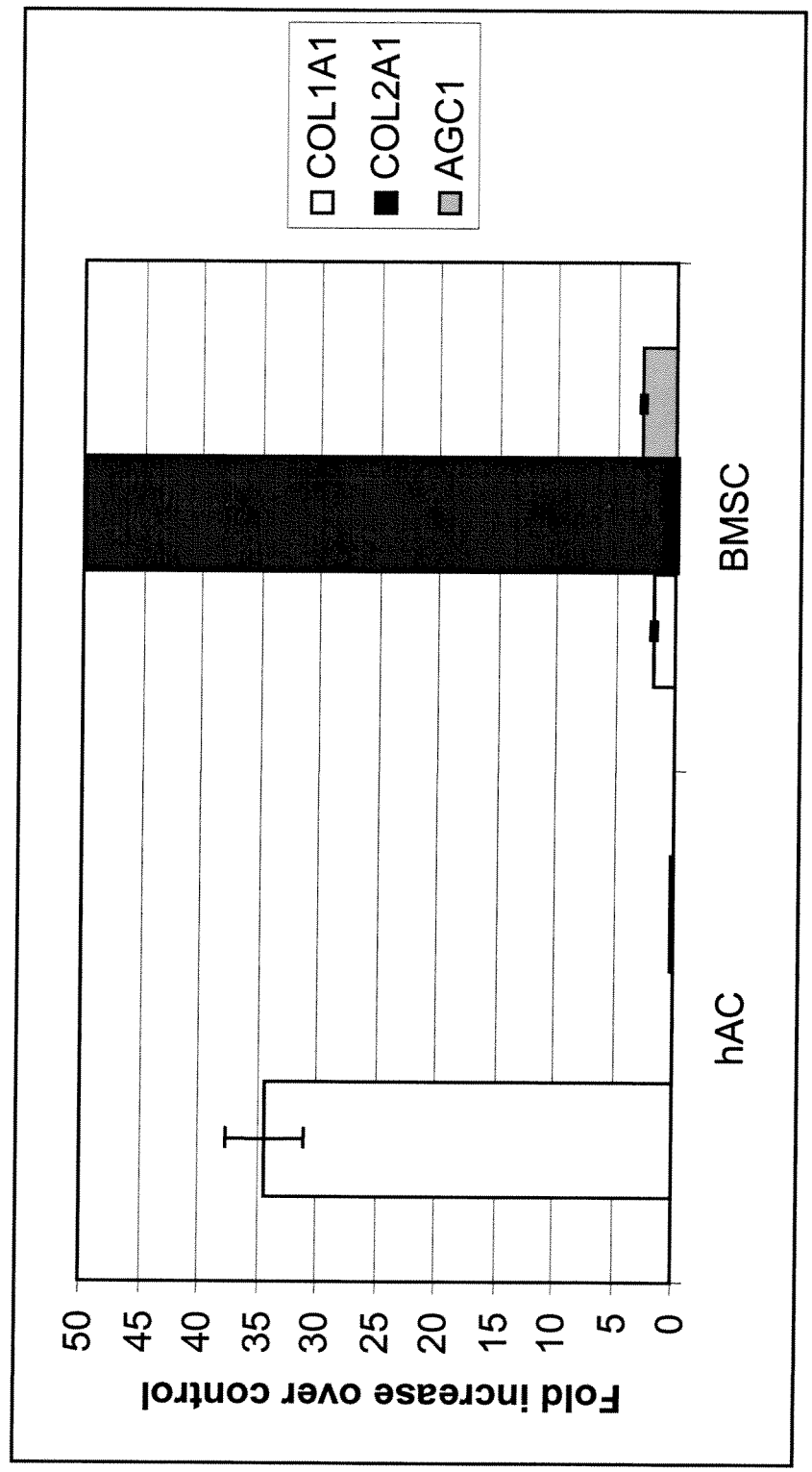
FIG. 6 is a graph illustrating gene expression, up-regulation of Type II collagen (COL 2A1) and down-regulation of Type I collagen (COL 1A1) mRNA production by bone marrow stem cells (BMSC) that migrated into DSTI compared to mRNA produced by human articular chondrocytes (hAC).

FIG. 6 shows differences between gene expression of bone marrow stem cells and human articular chondrocytes migrated into the DSTI. The bone marrow stem cells that migrate into DSTI in the presence of chondrogenic medium show increases in gene expression of Type II collagen (COL 2A1) and aggrecan (AGC1) whereas human articular chondrocytes begin to show signs of dedifferentiation leading to an increase in Type I collagen (COL 1A1) and decreases in Type II collagen (COL 2A1) and aggrecan (AGC1). Gene expression for bone marrow stem cells migrated into the DSTI is approximately 50 times higher that for human articular chondrocytes.

These data indicate a role of the DSTI in the modulation of the bone marrow stem cells differentiation as they populate and adhere within a 3D support structure.

G. DSTI as Chemoattractant for Bone Marrow Stem Cells

The DSTI possess a unique chemoattractive property for bone marrow stem cells that migrate toward and into the DSTI The potential for the DSTI to act as a chemoattractant for bone marrow stem cells was studied. To determine if cells will migrate across the Boyden Chamber in response to the presence of the DSTI, cell were seeded in the Boyden chamber and processed according to Example 9. Three different culture media, namely bovine serum albumin (BSA), growth (Growth) and chondrogenic (CCM) medium, were used for this study to explore possibility of enhancing the chemoattraction by using different culture medium. Results are seen on FIG. 7.

Figure 7:
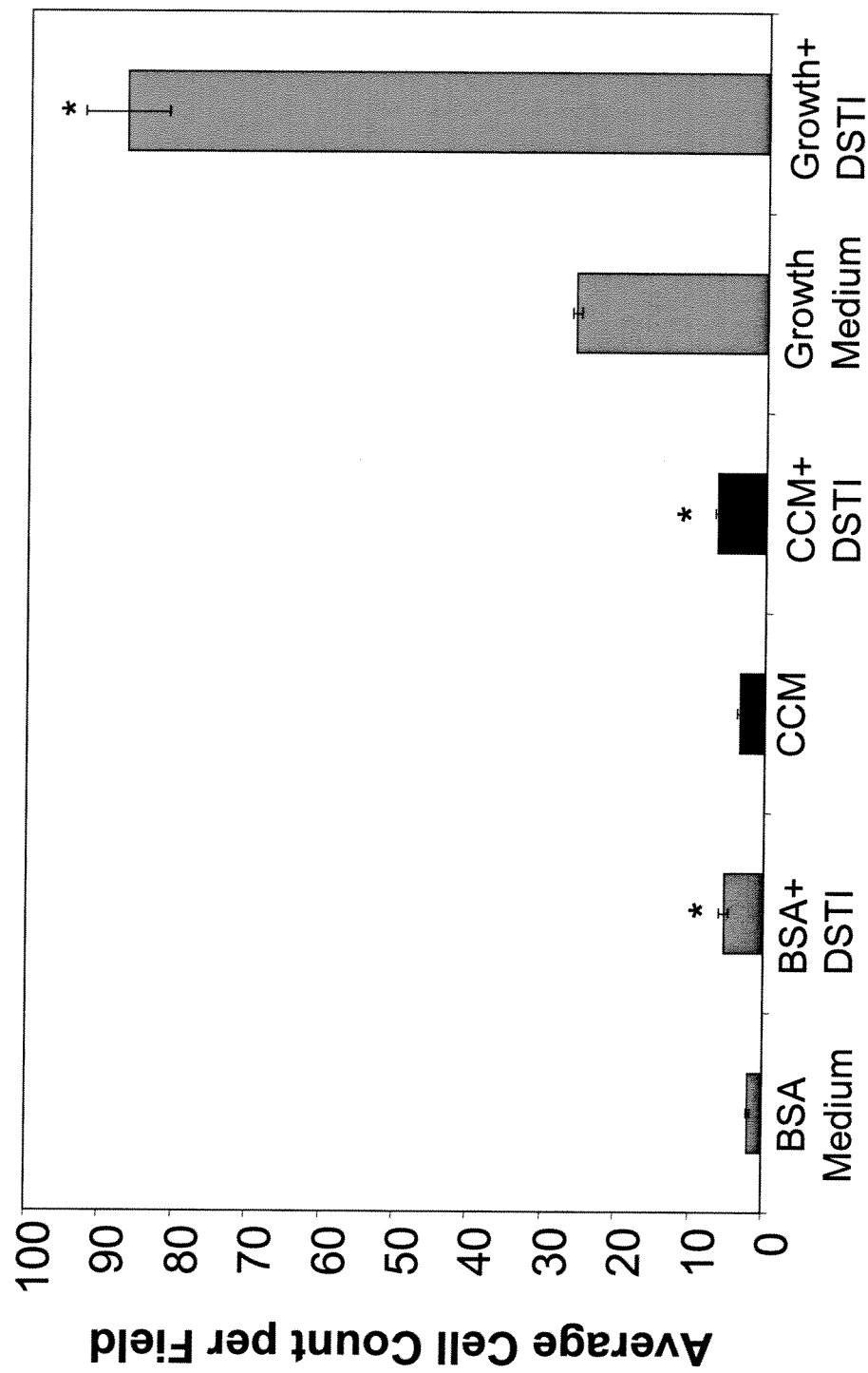
FIG. 7 is a graph illustrating chemoattractant properties of DSTI for bone marrow stem cells. The FIG. 7 shows a chemotactic activity of BMSC in response to various culture media formulations in the presence or absence of DSTI. Bovine serum albumin (BSA), chondrogenic (CCM) and growth (Growth) media were used with or without DSTI to determine chemoattractant property of the DSTI. Chemoattractant property of DSTI is expressed as an average increase in cell count per field.

FIG. 7 shows chemotactic activity of bone marrow stem cells in response to various culture media formulations and in the presence or absence of DSTI. As seen in FIG. 7, when the DSTI contained 1% BSA medium or the chondrogenic media, there were 2 or less cells per field. No difference was observed between the empty chambers and chamber containing DSTI. Number of cells/field increased somehow in the growth medium without DSTI when compared to the BSA and chondrogenic medium. However, the presence of DSTI containing a growth medium showed remarkable increase in the cell number/field. Specifically, in the presence of growth medium without DSTIs number of cells/field averaged 17.5 cells compared to number of cells/field observed in the presence of DSTI containing the growth medium where the number of cells/field averaged almost 90 cells. As seen in FIG. 7, there was a highly significant difference between the DSTI containing samples and the empty samples containing only the media for all three media. The 1% BSA medium showed a 2.8 fold increase in cells/field in the presence of DSTI compared to the medium alone without DSTI. The chondrogenic medium showed a 1.9 fold increase in cells/field for chambers containing DSTIs. The growth medium showed a 3.5+ fold increase in cells/field in chambers containing DSTIs.

This study clearly demonstrated that bone marrow stem cells are highly attracted to DSTI. Significantly more cells penetrated the Boyden Chamber membrane in response to the DSTI presence. Selection of media was able to further accentuate such attraction. Showing that such attraction may be manipulated by media selection and that it is particularly enhanced with use of the growth medium but not with chondrogenic medium indicates that such manipulation may be advantageously utilized for provoking or suppressing chemoattraction of DSTI.

H. The Double-Structured Tissue Implant Containing Cell Modulator

The double-structured implant of the invention, as shown above, has properties never before observed or described in any other tissue implant. One other important property is its variability of uses due to its double structure.

One embodiment of the DSTI use is the DSTI containing a cell modulator. The cell modulator may be a pharmaceutical agent, drug, growth modulator, growth hormone, mediator, enzyme promoting cell incorporation, cell proliferation or cell division, pharmaceutically acceptable excipient, additive, buffer, etc., incorporated into the primary or secondary scaffold, or to both scaffolds.

Any of the above mentioned compound may be introduced separately into the primary scaffold or into the secondary scaffold at a time of its formation by simply introducing such compound to the dehydrated dry DSTI. In alternative, such compound may be added to the DSTI at a time of rehydration before its implantation.

Suitable pharmaceutical agents, drugs or modulators are selected from the group consisting of:

growth and morphogenic factors, such as, for example, transforming growth factor, insulin-like growth factor 1, platelet-derived growth factor, bone morphogenetic proteins (bmps);

cytokines, such as, for example, interleukins, chemokines, macrophage, chemoattractant factors, cytokine-induced neutrophil chemoattractants (gro-1), integral membrane proteins such as integrins and growth factor receptors;

membrane associated factors that promote growth and morphogenesis, such as, for example, repulsive guidance molecules;

cell attachment or adhesion proteins, such as, for example, fibronectin and chondronectin;

hormones, such as, for example, growth hormone, insulin and thyroxine;

pericellular matrix molecules, such as perlecan, syndecan, small leucine-rich proteoglycans and fibromodulin;

nutrients, such as, for example, glucose and glucosamine;

nucleic acids, such as, for example, RNA and DNA;

anti-neoplastic agents, such as, for example, methotrexate and aminopterin;

vitamins, such as, for example, ascorbate and retinoic acid;

anti-inflammatory agents, such as, for example, naproxen sodium, salicylic acid, diclofenac and ibuprofen;

enzymes, such as, for example, phosphorylase, sulfatase and kinase; and metabolic inhibitors, such as, for example, RNAi, cycloheximide and steroids.

These, and other similar compounds and/or compounds belonging to the above-identified groups may be added individually or in combination to a primary scaffold, to a secondary scaffold, to a composition (Basic Solution) for formation of the secondary scaffold or to the lyophilized composite or DSTI before, during or after implantation.

Addition of agents such as growth factors, cytokines and chemokines will increase cell migration, cell growth, will maintain or promote appropriate cell phenotype and will stimulate extracellular matrix synthesis. Loading the scaffold with anti-inflammatory agents or other drugs can provide a local site-specific delivery system.

The range of concentration of the added drug or compound depends on the drug or compound and its function and it extends from picograms to milligrams.

I. Differentiation of Mesenchymal Stem Cells

DSTI is a novel implant that has chemoattraction for mesenchymal stem cells as well as for bone marrow stem cells that migrate into the DSTI. Such migration further results in differentiation of these cells and in their transformation into specifically functioning cells, such as, for example, chondrocytes. These properties were shown to be enhancible by using selected media as well as by complementing such media with compounds such as growth factors, pharmaceutical agents or growth modulators.

To confirm results obtained above that indicated that by using DSTI, differentiation of mesenchymal stem cells may be achieved and further improved by addition of growth factors, migration of mesenchymal stem cells (MSC) towards DSTI loaded with a repulsive guidance molecule (RGMA) that alters utilization of protein morphogenetic protein was studied.

Purpose of this study was to determine if DSTI loaded with a growth factor such as RGMA will increase the chemoattraction of the DSTI. In the above described studies on migration, it was determined that the DSTI possesses chemotactic properties towards BMSC and hAC. Although the results obtained above indicated that the migration of such cells increased in culture containing DSTI and growth factor containing medium, it was not known if the addition of a growth factor could also enhance the cell differentiation.

For this purpose, cells were tested in the Boyden Chamber according to a protocol of Example 10 in the presence and absence of repulsive guidance molecule (RGMA) with or without DSTI in the culture for 18 hours. Results are seen in FIG. 8.

Figure 8:
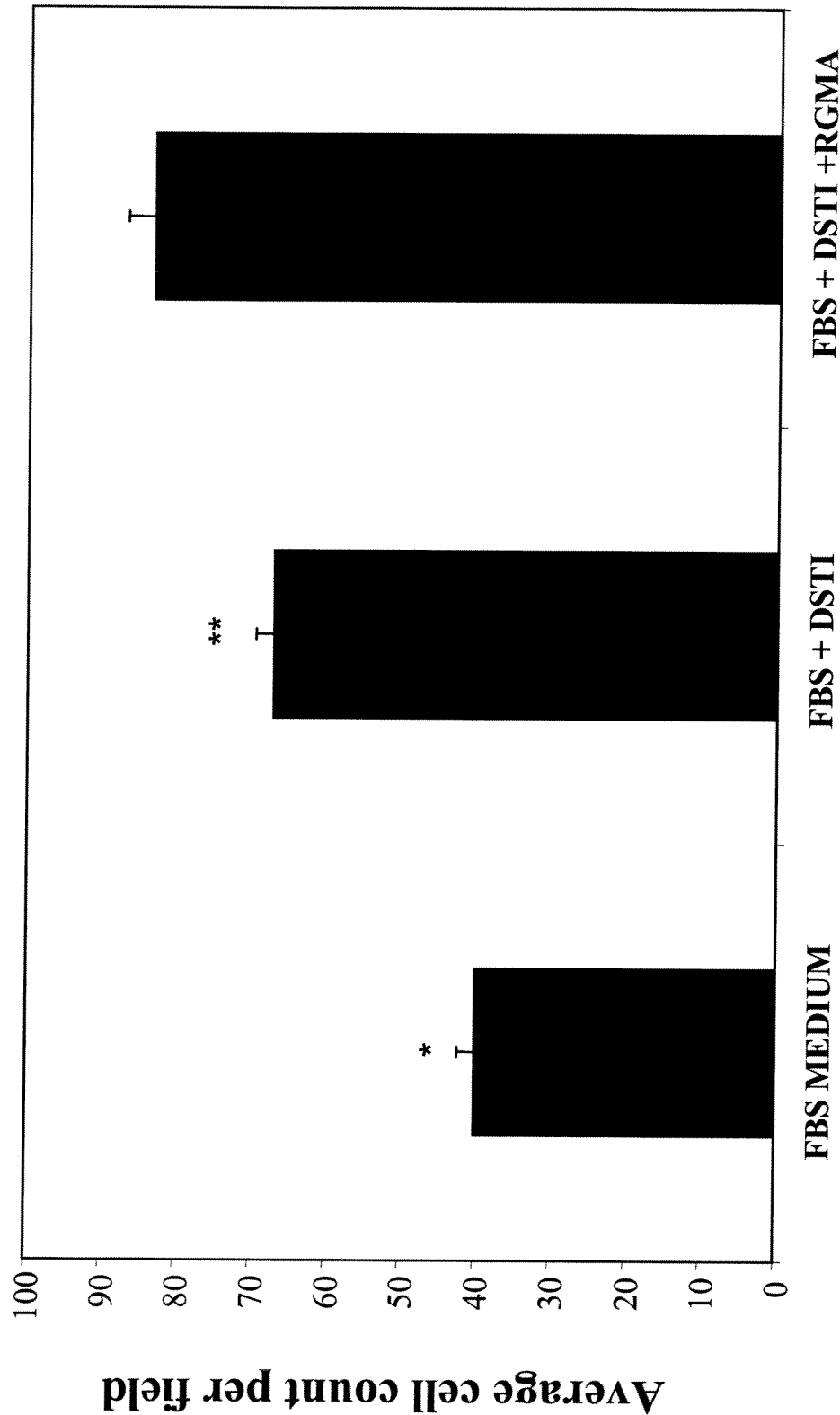
FIG. 8 is a graph illustrating the chemoattractant property of DSTI that can be enhanced by the addition of a growth factor, namely repulsive guidance molecule (RGMA). Fetal bovine serum (FBS) medium was used as a control against the DSTI containing FBS medium and DSTI containing FBS medium and RGMA.

FIG. 8 shows average cell count per field is samples of medium only, DSTI containing medium and DSTI containing medium and RGMA. Results seen in FIG. 8 show that in 18 hours, the presence of DSTI signifiantly ($p<0.00001$) increased migration of BMSC by approximately 1.7 times in DSTI containing the FBS medium when compared to samples containing only the FBS medium. The addition RGMA to DSTI further significantly ($p<0.000001$) increased cell count 2.1 times when compared to samples containing only FBS medium. An increase in average cell count per field also increased ($p<0.002$) compared to DSTI containing the medium without RGMA.

This study confirmed that DSTI is chemoattractive to MSC and that this effect can be advantageously enhanced by the addition of a growth factor such as RGMA.

Further studies were directed to determination if migration of MSC towards DSTI loaded with other growth factors also initiates differentiation gene expression.

For this purpose, the potential morphogenetic factors RGMA, BMP-2 and BMP-7 were investigated for their ability to initiate gene expression relating to MSC differentiation and maintenance of chondrocytes.

Initial studies on RGMA have demonstrated not only its ability to enhance chemoattraction to DSTI but also its ability to up-regulate BMP-2 gene expression in both chondrocytes and MSCs. BMP-2 and BMP-7 have been well documented to act as growth factors that induce cartilage production. This study was designed to compare these three potential growth factors on their ability to increase initiation of MSC differentiation and maintenance of chondrocytes.

Human bone marrow mesenchymal stem cells (MSC) were subjected to treatment in Boyden Chamber assay in the absence (empty) or presence of DSTI (DSTI), DSTI and RGMA (RGMA), DSTI and BMP-2 (BMP-2) and BMP-7 and DSTI (BMP-7). At intervals of 72 hours and three weeks, samples of DSTI were tested for RNA production for RT-PCR (72 hours) and for production of RNA and subjected to histological analyses.

Figure 9:
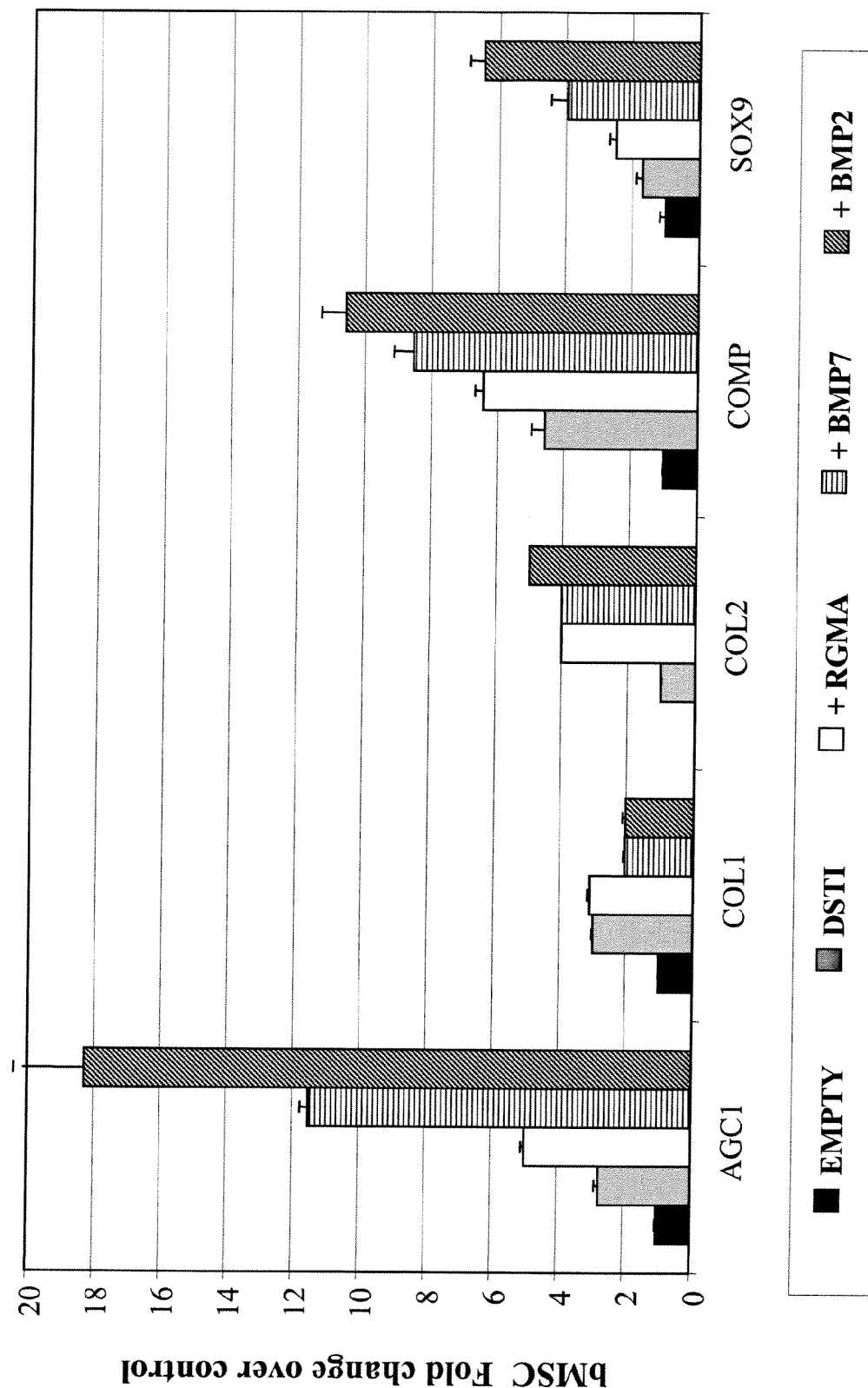
FIG. 9 is a graph illustrating up-regulation of cartilage specific genes determined by the levels of mRNA for protein aggrecan (AGC1), collagen Type I (COL 1A1), collagen Type II (COL 2A1), cartilage oligomeric matrix protein (COMP), and the chondrogenic transcription factor SOX9 by bone marrow mesenchymal stem cell (BMSC) migration toward DSTI containing the chondrocyte growth medium and growth factors RGMA, BMP-2 and BMP-7 compared to DSTI containing the chondrocyte growth medium without the growth factor (DSTI) and to the chondrocyte growth medium only without DSTI and growth factor (Empty).
Figure 10:
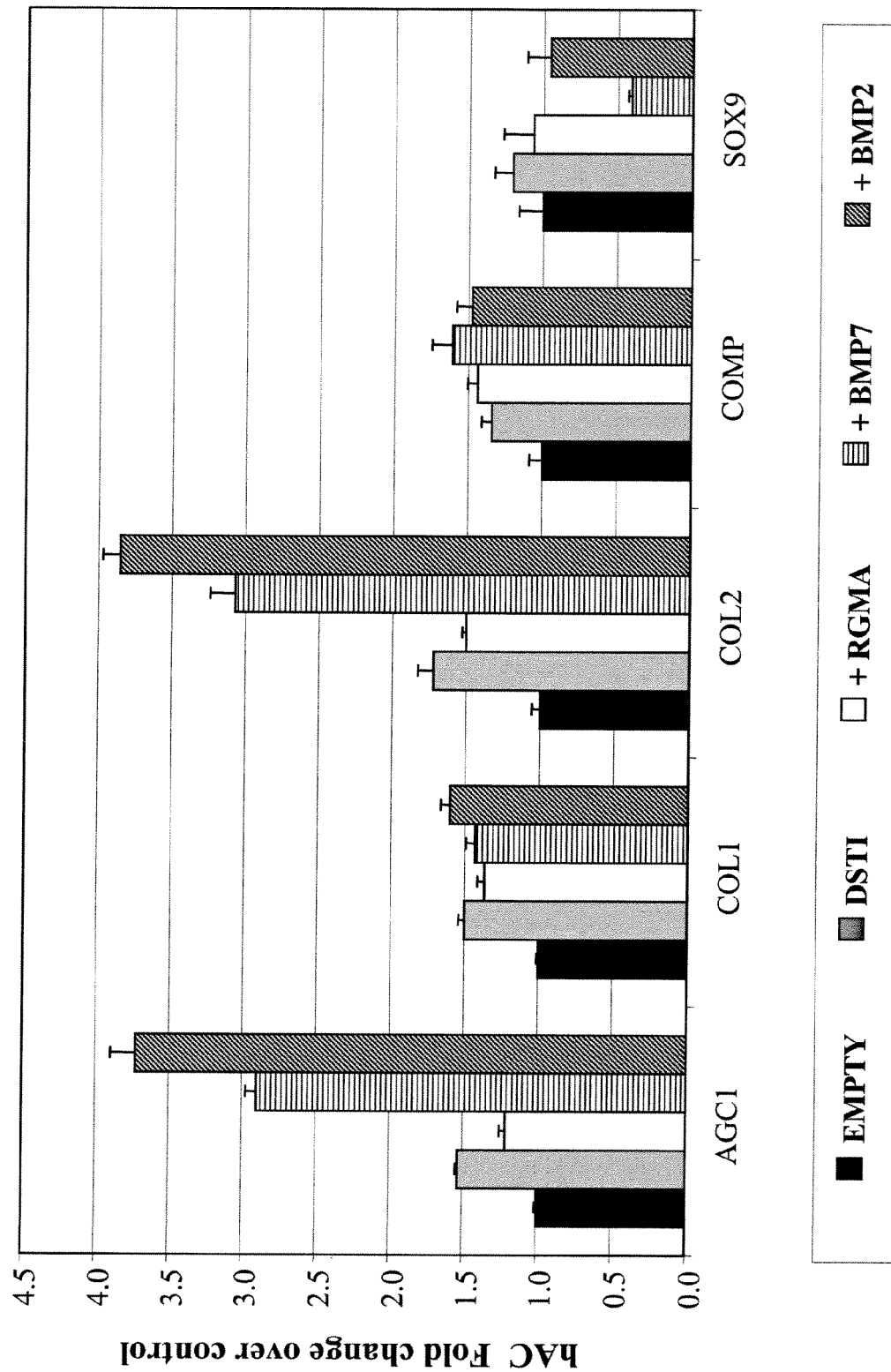
FIG. 10 is a graph illustrating up-regulation of cartilage specific genes determined by the levels of mRNA for protein aggrecan (AGC1), collagen Type I (COL 1A1), collagen Type II (COL 2A1), cartilage oligomeric matrix protein (COMP), and the chondrogenic transcription factor SOX9 by human articular chondrocytes migrated toward DSTI containing the chondrocyte growth medium and growth factors RGMA, BMP-2 and BMP-7 compared to DSTI containing the chondrocyte growth medium without the growth factor (DSTI) and to the chondrocyte growth medium only without DSTI and growth factor (Empty).

Results are seen in FIGS. 9 and 10. FIG. 9 shows results obtained with mesenchymal stem cells. FIG. 10 shows results obtained with human articular chondrocytes. RT-PCR analysis of the 72 hour experiments showed that MSC (FIG. 9) migrating towards DSTI show significantly increased production of aggrecan (AGC1) and cartilage oligomeric matrix protein (COMP) expression, whereas hAC (FIG. 10) did not have similar increases (note a different scale). RGMA, BMP-7, and BMP-2 displayed increasing expression, respectively, when compared to DSTI in FIG. 9 for MSC for AGC1, COL 1A1, COMP, and a chondrogenic transcription factor SOX9. hAC showed similar increases in AGC1 and COL2A1 in response to BMP-2 and BMP-7 only (FIG. 10).

The results shown in FIGS. 9 and 10 show that migration of MSC towards DSTI containing growth factors up-regulates cartilage specific genes, such as COMP and SOX9. Migration of hAC towards DSTI containing growth factor maintains chondrocyte phenotype. Migration of MSC (FIG. 9) toward DSTI leads to chondrocytic gene expression up-regulation. The addition of a growth factor such as RGMA, BMP-7 or BMP-2 to DSTI enhances this gene up-regulation at 72 hours. Chondrocytes (FIG. 10) maintain their phenotype in response to migration towards DSTI combined with growth factors.

These studies showed that BMP-2-stimulated MSC show increased production of AGC1, COL2A1 and COMP, but that is also had significantly increased a bone gamma-carboxyglutamic acid protein (BGLAP) Such increase may be a possible indication of conversion to osteogenic phenotype. BMP-7 and RGMa show a similar increase in COL2A1 and COMP, but lack the increase in BGLAP. hAC subjected to similar analyses show a similar pattern of AGC11, COL2A1, and BGLAP increased expression when stimulated with BMP-2, with no apparent changes in response to RGMa or BMP-7.

J. The Effects of Hydrostatic Pressure on Chondrocyte Differentiation in DSTI

Previously, inventors discovered an effect of hydrostatic pressure on proliferation of articular chondrocytes in studies where the adjustment of hydrostatic pressure, culture medium perfusion and oxygen levels has been used to simulate the articular cartilage environment. Consequently, a purpose of this study was to investigate if similar conditions would enhance cells differentiation and growth in the DSTI. This study investigates the effect of hydrostatic pressure and low oxygen on bone marrow stem cells differentiation potential in DSTI.

Briefly, bone marrow stem cells and human articular chondrocytes were subjected to culturing conditions under either the hydrostatic pressure or the static pressure. The tissue engineering processor (TEP) and chondrogenic medium were used to investigate the role of hydrostatic pressure on differentiation of bone marrow stem cells seeded into DSTI. The protocol used for this study is described in Example 13. Results are seen in FIG. 11.

Figure 11:
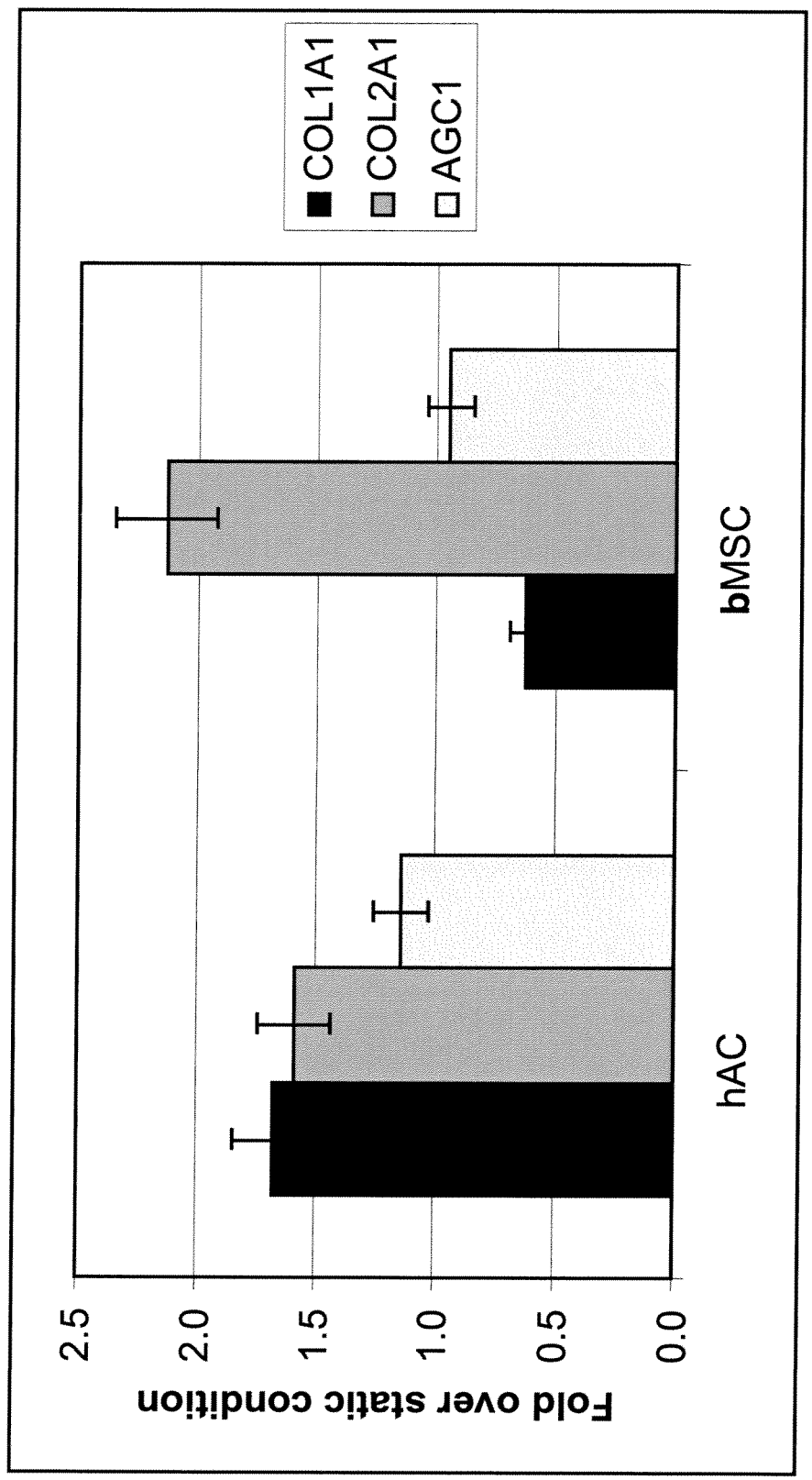
FIG. 11 is a graph showing an effect of hydrostatic pressure on production of mRNA for Type I collagen (COL 1A1), Type II collagen (COL 2A1) and aggrecan (AGC1) for human articular chondrocytes (hAC) and bone marrow stem cells (BMSC). The effect of the hydrostatic pressure is expressed as increase in mRNA over levels observed at static pressure.

FIG. 11 shows that hydrostatic pressure increases production of Type II collagen and depresses production of Type I collagen gene expression. Hydrostatic pressure protocol generated by (TEP leads to stimulation of both cell types compared to static cultures. Bone marrow stem cells leads to increased expression of Type II collagen and decrease of Type I collagen.

Real time RT-PCR data show that human articular chondrocytes do relatively well in TEP compared to static conditions, where COL 2A1 and AGC1 remained elevated. Bone marrow stem cells showed an increase in COL 2A1 and a decrease in COL 1A1 with relatively no change in AGC1 expression.

K. Properties of the Double-Structured Tissue Implant

Double-structured tissue implant of the invention has chemoattractant, cell adhesion, wettability, shape-memory and structural stability properties for cells, stem cells, mesenchymal stem cells and bone marrow stem cells.

These properties were demonstrated in the above studies. The double structure of the implant provides structural stability, wettability and possess a shape-memory when hydrated. In addition, DSTI acts as a chemoattractant for bone marrow stem cells and for human articular chondrocytes. The above-described studies demonstrated that when the DSTI is brought into contact with bone marrow stems cells and/or human articular chondrocytes, such cells migrate into the DSTI, adhere to the DSTI double structure, differentiate and express the chondrocyte genotype and produce cartilage specific extracellular matrix. Moreover, such cell behavior may be advantageously modified and amplified by addition of cell modulators, by different culture media or by applying a hydrostatic pressure and other culture conditions. By using DSTI for seeding of cells or as a recipient of the cell migration, the differentiation of bone marrow stems cells into the chondrocyte genotype is enhanced.

DSTI, therefore, is a suitable implant that supports both human articular chondrocyte and bone marrow mesenchymal stem cell adhesion as well as their proliferation. Upon implantation of DSTI in a chondral defect with the addition of bone marrow stem cells, the joint environment will facilitate differentiation into the chondrocyte phenotype. The DSTI as an implant is therefore eminently suitable for repair of chondral or other tissue defects. Use for repair of the muscle, vascular, cardiac or neural tissue may be accomplished by directing the stem cells, mesenchymal stem cells, bone marrow stem cells or neural stem cells to differentiate into muscle, cardiac, epithelial or nerve cells.

III. Process for Preparation and Use of the Double-Structured Tissue Implant

The secondary scaffold is generated within confines of the primary scaffold by a process comprising several stages and steps as set forth in Scheme 1. The process stages comprise pre-loading, loading, polymerization, treatment of composite double-structured scaffold, dehydrothermal treatment, packaging and, ultimately, its surgical delivery.

SCHEME 1

Process for Production and Use of a Double-Structured Implant

Stage 1—Pre-Loading

The pre-loading stage is a preparatory stage where the primary scaffold is either obtained from commercial sources or is prepared according to the procedure described in Example 1.

Step 1

Step 1 comprises obtaining or preparing a primary scaffold, typically a collagen containing honeycomb, sponge or lattice providing a structural support for incorporation of the secondary scaffold.

In one embodiment, a bovine Type I collagen matrix with honeycomb (HC) like structure is obtained, for example, from Koken, Inc. (Japan) or from other commercial sources and used as primary scaffold. However, such commercially available honeycomb matrices have typically randomly distributed pores of irregular shape and size. The pores of these structures are not always vertically positioned.

In another embodiment, and preferably, a primary honeycomb scaffold is produced according to a process described in Example 1, wherein said primary scaffold has randomly or non-randomly oriented pores of substantially the same size and shape.

The shape and size of the primary scaffold determines a size of the double-structured tissue implant (DSTI) ultimately delivered to the surgeon for implantation into the tissue defect.

Typically the DSTI has a rectangular, circular or oval shape with dimensions of about 50 mm and a vertical thickness of about 1 to 5 mm, preferable 1-2 mm. Preferred dimensions of the DSTI and, therefore, the dimensions of the primary scaffold are 50×50 mm×1.5 mm, with pores oriented substantially vertically, said pores having a pore size of from about 100 to about 400 µm, preferably about 200±100 µm and pore length of 1.5 mm. However, dimensions of the primary scaffold may be any that are required by the tissue defect to be repaired and that can be prepared by the process of the invention.

Step 2

Step 2 comprises preparing a composition for preparation of a secondary scaffold (Basic Solution) and comprises neutralization of a soluble collagen solution having an initial acidic pH of about pH 1.5-4, preferably between about pH 1.9-2.2, a collagen concentration from about 0.5 to about 10 mg/ml of collagen, preferably about 2.9 to about 3.2 mg/ml, a surfactant concentration from about 0.05 to about 10 mg/ml, preferably about 0.29 to about 0.32 mg/ml and osmolality from about 20 to about 400 mOsm/kg, preferably about 280 to about 320 mOsm/kg. The soluble collagen solution is then neutralized with any suitable base and/or buffer to pH in a range from about pH 7.3 to about pH 7.7 to derive the Basic Solution. Preferably, the solution is neutralized by adjusting pH to neutrality 7.4 using a collagen/surfactant, 10× Dulbecco phosphate buffered saline (DPBS) and 0.1 M NaOH in 8:1:1 ratio or using an aqueous solution or ammonia vapor in concentration sufficient to neutralize acid within the collagen solution. The final osmolality and pH of the Basic Solution is about 290 mOsm/kg and pH 7.4, respectively.

The suitable buffers for solubilization of the Type I collagen are, for example, a formic acid containing buffer at pH 4.8, acetic acid containing buffer at pH 5.0 or a diluted hydrochloric acid containing buffer at pH 3.0.

Neutralization is typically carried out using ammonia aqueous solution or a vapor of about 0.3%-1% ammonia, or in concentration sufficient to neutralize the acidic pH over about 12 to about 24 hour period. This factor has also been found to affect the collagen polymerization and formation of pores having homogeneous pore size.

Stage 2—Loading and Precipitation

The primary scaffold is loaded with a Basic Solution for the secondary scaffold comprising soluble collagen solution containing a surfactant. This Basic Solution is subsequently precipitated within pores of the primary scaffold.

Loading the primary scaffold with the Basic Solution for the secondary scaffold is performed using any suitable method. Soaking, wicking, submerging the primary scaffold in the solution, electrophoresis and any other suitable means. Once the Basic Solution for the secondary scaffold is introduced into the primary scaffold, a composite of both is subjected to a process or treatment that results in formation of the secondary scaffold inside pores of the primary scaffold.

Step 3

The neutralized Basic Solution of step 2 is loaded into the primary scaffold by placing from about 3.75 to about 7.5 ml (approximately 1 to 2×volume), preferably a volume about 4.9 ml (approx. 1.3×volume of the primary scaffold) of the secondary scaffold Basic Solution on the bottom of a dish and then placing the primary scaffold in this solution and allowing it to be soaked up.

Stage 3—Polymerization of the Soluble Collagen within a Primary Scaffold into a Secondary Scaffold The primary scaffold loaded with the neutralized Basic Solution comprising the soluble collagen and the surfactant is then subjected to conditions resulting in precipitation of the neutralized Basic Solution within the pores of the primary scaffold thereby generating a structurally distinct secondary scaffold.

Typically, and allowing for variability of the Basic Solution or composition used for creating of the secondary scaffold, the composition introduced into the pores of the primary scaffold is gelled or precipitated within said primary scaffold and may also be cross-linked using chemicals such as glutaraldehyde or another multifunctional aldehyde, where the aldehyde reacts with amino groups of the collagen yielding a Schiff base, which can be stabilized by a reduction reaction; carbodiimide reagent, such as carbodiimide 1-ethyl-3-(3-dimethyl aminopropyl)-carbodiimide (EDC) with or without N-hydroxy-succinimide (NHS) where the HNS is used to suppress side reactions. Additionally, EDC and NHS can be used in combination with diamine or diacid compounds to introduce extended cross-links; acyl azide where the acid are activated and subsequently reacted with an adjanced amine group; epoxy compounds such as 1.4-butanediol diglycidyl ether, or cyanamide.

In addition, irradiation such as short wave length UV irradiation (254 nm) can introduce cross-links in the collagen.

Step 4

The primary scaffold loaded with the neutralized collagen/surfactant solution in a range from about 1 to about 2 volumes of the primary scaffold is then placed in an incubator at a temperature from about 25° C. to about 38° C., preferably to about 37° C. temperature, typically for from about 10 minutes to about 18 hours, more typically for about 20 to about 100 minutes, preferably for about 40 to 60 minutes, and most preferably for a time when the precipitation of the neutralized collagen solution into a solid secondary scaffold occurs.

Step 5

In order to assure that the vast majority of the salt of the precipitated collagen solution within the pores of the primary scaffold is removed, a composite consisting of the primary scaffold having the secondary scaffold precipitated within is subjected to a washing step whereby the majority of the salts are removed.

The composite (Composite) comprising the primary scaffold and the secondary scaffold precipitated within, is washed by placing said composite in a volume of from about 20 ml to about 10 liters, preferably about 500 ml, of de-ionized water further containing a non-ionic surfactant. The surfactant is typically present in concentration from about 0.05 to about 1.0 mg/ml, preferably about 0.23 mg/ml. Most preferred surfactant is PLURONIC® F127.

Typically, the washing step takes approximately 30 minutes. There may be one or several washing step repetitions. All excess non-precipitated collagen is removed during the extraction from the composite into the wash solution.

Polymerizing of the collagen present in the secondary scaffold solution loaded within the primary scaffold pores results in formation of a solid double-structured composite, as defined above, comprising the primary scaffold and the secondary scaffold precipitated therewithin.

Following the precipitation or gelling and washing, the composite is subjected to lyophilization and dehydrothermal treatment.

Stage 4—Dehydration of Composite Double-Structured Scaffold

The solid double-structured composite is then dehydrated using any method suitable for such dehydration. Typically, such dehydration will be freeze-drying or lyophilization. Freezing is typically carried out at temperature from about −10° C. to about −210° C., preferably from about −80° C., over a period of about 2 to about 60 minutes. The frozen composite is then lyophilized forming the Lyophilized Composite.

The gradual nature of the polymerization and slow process f water removal typically maintains the architectural elements of the secondary scaffold and achieves the proper orientation and diameter of the pores.

Step 6

Freezing is achieved with freezing the solid double-structured composite by placing it on the metal shelf of a freezer and adjusting the temperature to from about −10° C. to about −210° C., preferably to about −60° C. to about −90° C., and most preferably for about −80° C., for about 2 to about 60 minutes, preferably for about 20-45 minutes and most preferably for about 30 minutes.

Step 7

The frozen solid double-structured composite is then subjected to lyophilization. The frozen composite is removed from the freezer and placed into a pre-cooled lyophilization chamber. Lyophilization typically occurs in about 15-21 hours, depending on the size and shape of the composite but is typically and preferably completed in about 18 hours.

Stage 5—Dehydrothermal Treatment

To further stabilize the composite to provide resistance to dissolution and to achieve sterility of the final product, the solid double-structured composite is subjected to dehydrothermal (DHT) treatment. DHT treatment achieves cross-linking of the collagen with the surfactant and at higher temperatures also sterilizes the DSTI.

Cross-linking step prevents dissolution of the secondary scaffold upon rehydration before or after implantation.

Step 8

This step is performed to sterilize and cross-link the double structured tissue implant.

The lyophilized double-structured composite is placed into a dry glass chamber or container and covered with the glass, aluminum foil or another suitable material resistant to higher temperatures. The container with the lyophilized double-structured composite is placed into the pre-heated dehydrothermal oven and subjected to a temperature in a range from about 70° C. to about 200° C., preferably from about 130° C. to about 150° C., and most preferably about 135° C., under vacuum, for about 30 minutes to about 7 days, preferably for about 5-7 hours and most preferably for about 6 hours.

Such treatment stabilizes the composite, makes it resistant to collagen dissolution upon wetting, provides for rapid wetting and assures none or minimal shrinkage or swelling upon wetting with a physiological solution or buffer, and sterilizes the double-structured tissue implant.

Stage 6—Packaging and Storage

The double-structured tissue implant fabricated by the process described above is then ready for a sterile packaging and storage. In this form, the DSTI has a long shelf-life.

Step 9

The double structured tissue implant is removed from the dehydrothermal oven and transferred aseptically into sterile environment, such as a Bio Safety Cabinet (BSC), where it is packaged under conditions assuring sterility. The double-structured tissue implant is then ready to be stored at room temperature until its use.

Stage 7—Delivery by Implantation

Packaged double-structured tissue implant is delivered or made available to a surgeon for implantation into a tissue defect.

Step 10

During surgery, surgeon determines an extent of the defect or lesion to be repaired, opens the packaged product, cuts the DSTI to size of the defects and places the cut-to-size piece into said defect. Typically, the implant is placed into the defect in a dry form and a suitable physiologically acceptable solution is then added to wet the implant in situ. In alternative, the implant may be wetted before the implantation and then placed into the defect.

Since the implant is very stable, and does not change its size or shape significantly by shrinking or swelling, the implant fits tightly into the defect or lesion. To assure that the implant stays within the defect or lesion, such defect or lesion is first coated with a suitable tissue adhesive, sealant or glue that keeps the implant in place. In alternative, the defect or lesion may be pretreated with microfracture where the tissue underlying the lesion or defect is microfractured with microchannels to permit the blood and nutrient supply into the lesion or defect, lining the defect or lesion but not the microfracture, with the adhesive, glue or sealant and placing the implant as described above. In both instances, the implant placed into the lesion or defect may optionally be covered with another layer of the adhesive, sealant or glue.

In some instances, cells, drugs or modulators may be loaded into the DSTI or attached to the second scaffold before implantation and wetting, during wetting following the implantation, or independently provided after the implantation.

Results obtained for three separate lots containing three rehydrated DSTIs per each lot, are seen in Table 2. The DSTI is rehydrated by placing a droplet of phosphate buffer saline (1.5×volume of PBS), on top of the DSTI and the rehydration time is measured as the time it takes for the DSTI to be completely hydrated.

The pH of the rehydrated DSTI products is between 7.7 and 7.8 in all lots.

Osmolality of the rehydrated DSTI products is between 317 and 356 mOsm/kg in all lots.

Variation in size of rehydrated DSTI products is negligible evidencing that there is no shrinkage or swelling upon hydration of DSTI.

Collagen retention within the rehydrated DSTI is above 99%, evidencing a great stability of the DSTI products.

IV. Method of Use of Double-Structured Tissue Implant

Double-structured tissue implant of the invention is useful for treatment and repair of tissue defects of various tissues. Such treatment is achieved by implanting the DSTI into the defect in surgical setting with cells, stem cells, mesenchymal stem cells or bone marrow stem cells either added tot he DSTI by seeding said cells within the DSTI before or during surgery or by preparing a surgical site of the defect in such a way that said cells will naturally migrate into said DSTI due to tis chemoattractant properties.

In this regard, the use of DSTI for implantation is illustrated in FIGS. 12A-12E. These Figures illustrate, in a schematic way, implantation of DSTI into the articular cartilage lesion. However, the same or similar process would be used for implantation of the DSTI into defect of any other tissue.

FIGS. 12A-12F is a schematic illustration of several treatment protocols for implantation of the DSTI into a tissue lesions, exemplarized here with the implantation of the DSTI into the cartilage lesion, using a double-structured tissue implant (DSTI) containing stem cells, mesenchymals stem cells or bone marrow stem cells. These cells may be seeded within said DSTI with or without previous culture or activation or may migrate into the DSTI from the surrounding native tissue.

Figure 12A:
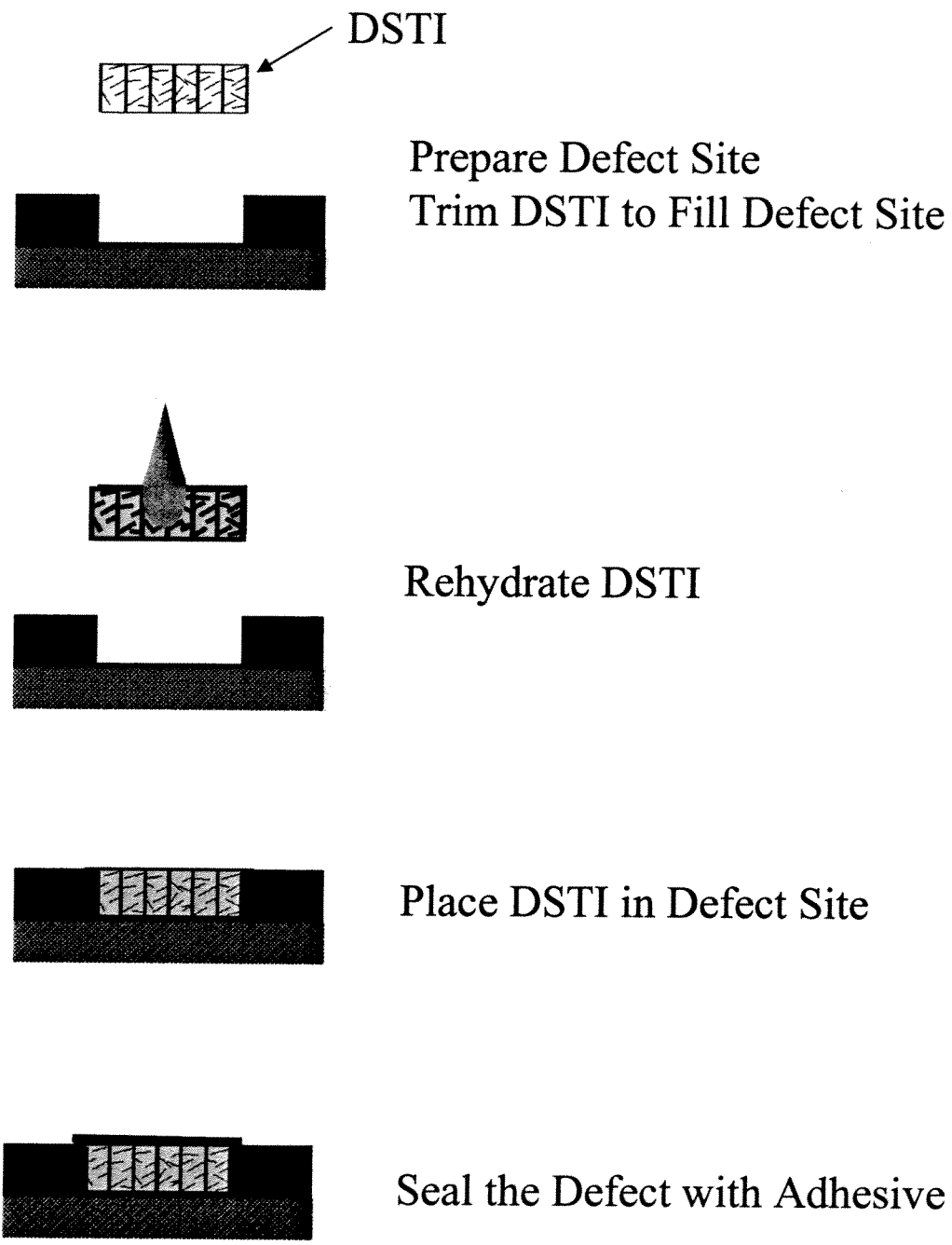
FIGS. 12A-12F are schematic illustrations of treatment protocols for implantation of the DSTI into cartilage lesions using double-structured tissue implants containing stem cells, mesenchymal stem cells or bone marrow stem cells.

FIGS. 12A-12F are schematic illustrations of treatment protocols for implantation of the DSTI into cartilage lesions using double-structured tissue implants containing mesenchymal stem cells or bone marrow stem cells. FIG. 12A is a schematic illustration of a method for implantation of DSTI into the tissue lesion or defect where the DSTI is provided as a dry DSTI, is precut and trimmed into the size and shape of the lesion, rehydrated with a physiologically acceptable solution that may contain non-differentiated or pre-differentiated stem cells or mesenchymal stem cells and the DSTI is placed into the lesion. Before rehydration, the stem or mesenchymal stem cells are first dissolved in a physiologically acceptable solution and such solution is applied to the dehydrated, pre-

TABLE 2

| Attribute | Number of Sample (n/lot) | Results | | |
|---|---|---|---|---|
| | | Lot #1 | Lot #2 | Lot #3 |
| Rehydration Time (seconds) | 3 | <2 | <2 | <2 |
| Rehydrated pH | 3 | 7.7 ± 0.1 | 7.8 ± 0 | 7.7 ± 0.1 |
| Rehydrated osmolality (mOsm/kg) | 3 | 317 ± 6 | 356 ± 4 | 319 ± 1 |
| Size variation at hydration (%) | 3 | 99.8% ± 5.2% | 100.6% ± 10.0% | 99.7% ± 2.3% |
| Collagen Retention in PBS (%) | 3 | 99.4% ± 0.2% | 99.1% ± 0.1% | 99.2% ± 0.2% |

As seen in Table 2, results obtained in three different lots in three different studies are closely similar confirming the reproducibility of the process as well as consistency of the parameters observed after rehydration.

Figure 12B:
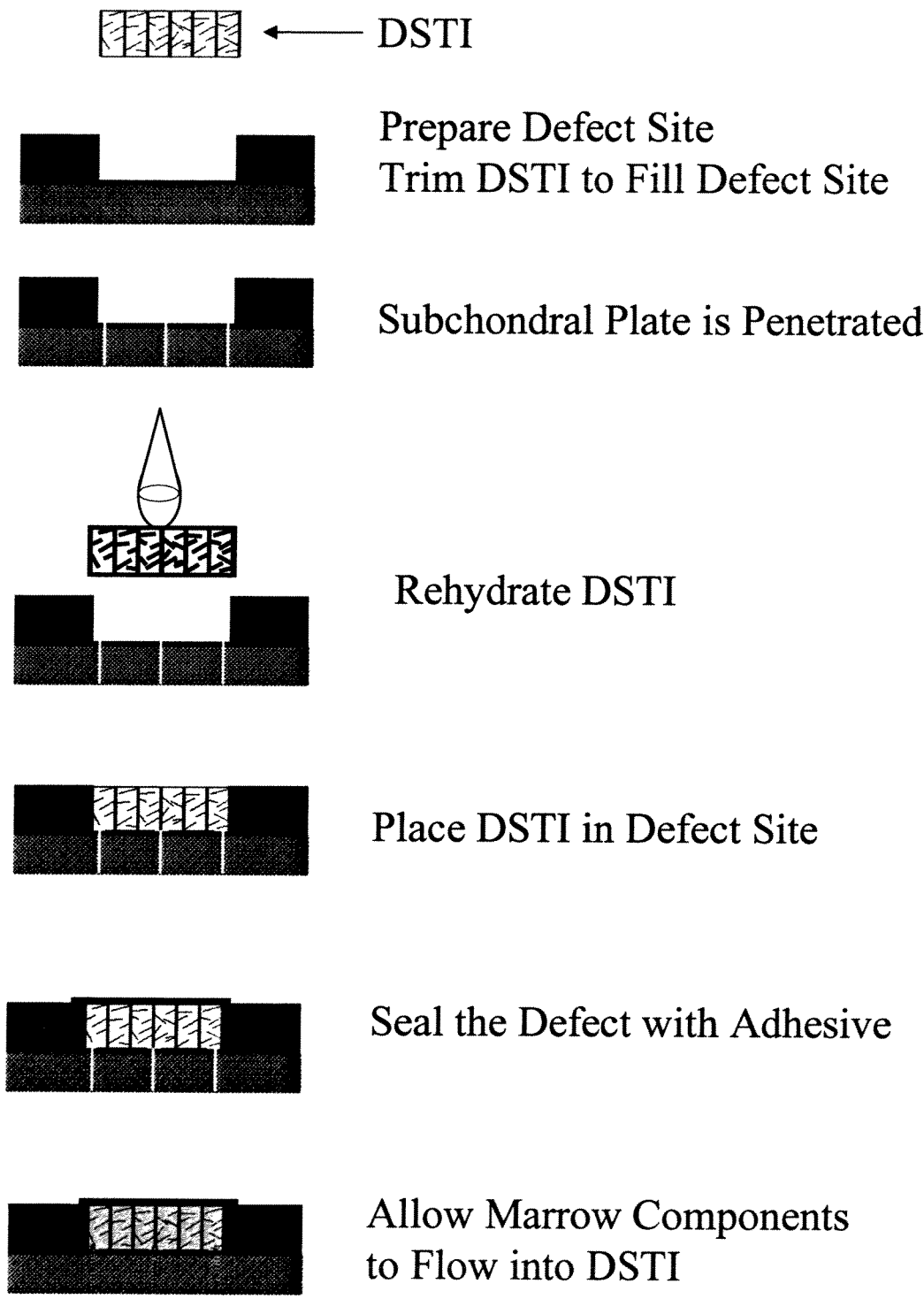
Figure 12C:
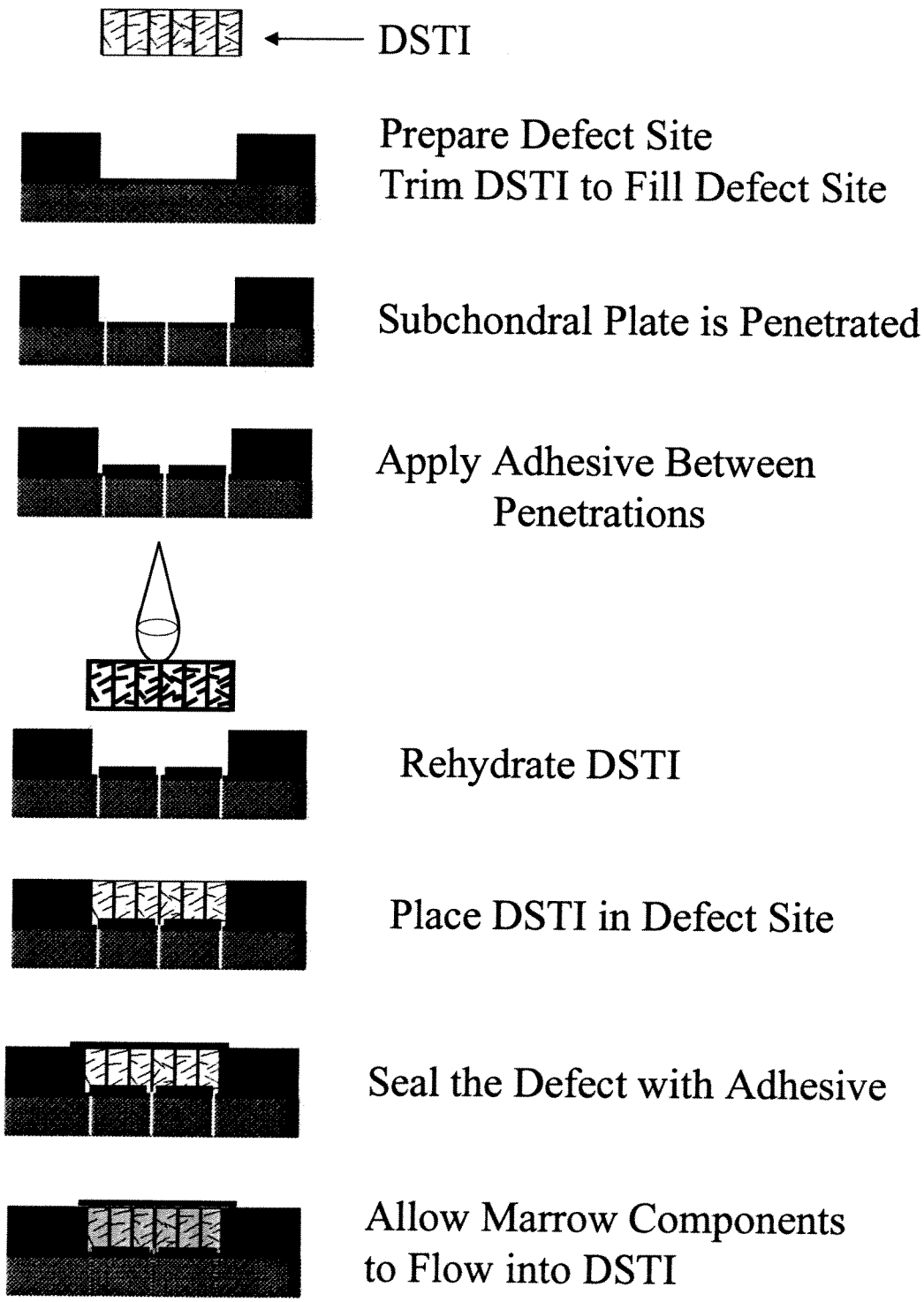
Figure 12D:
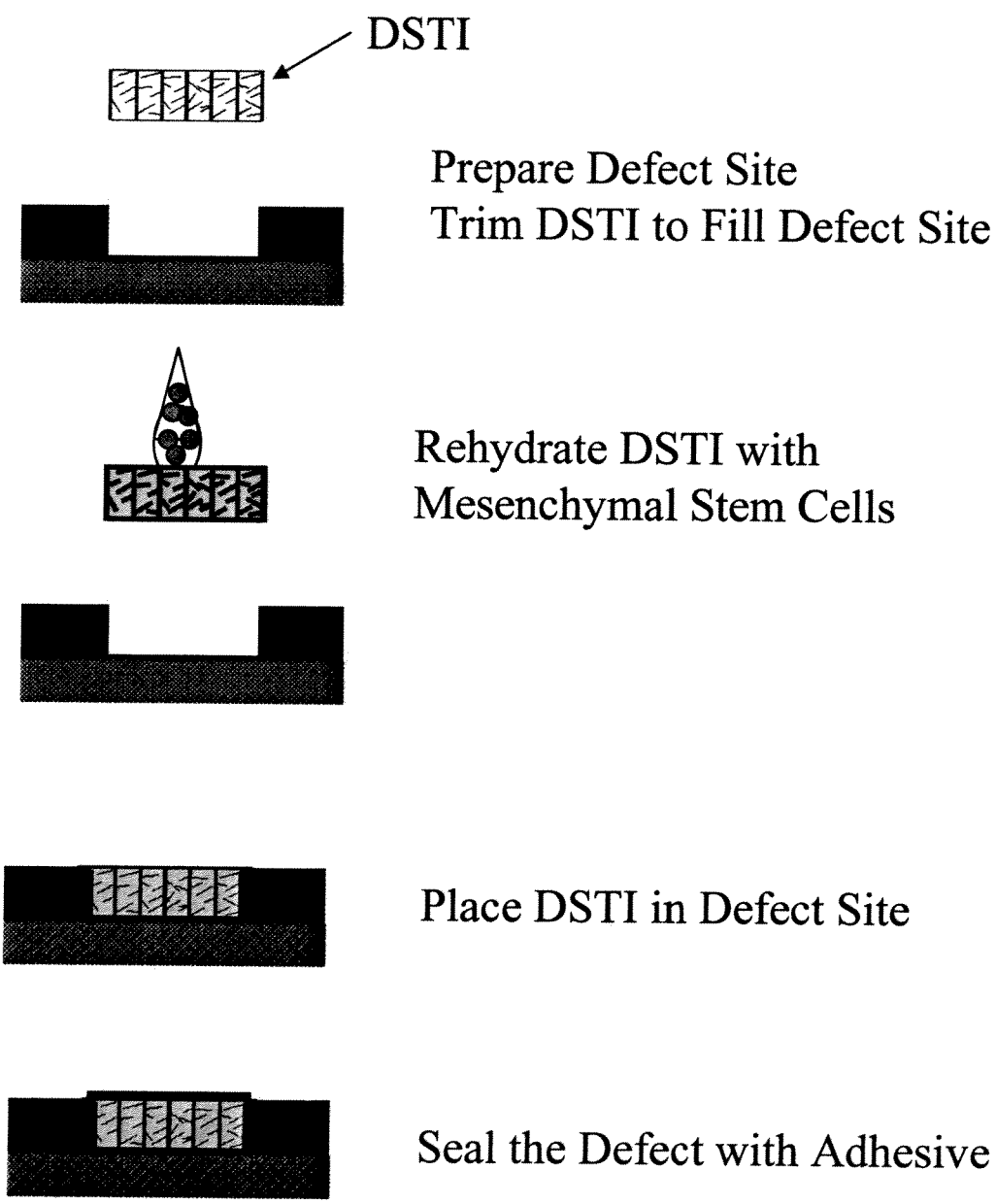
Figure 12E:
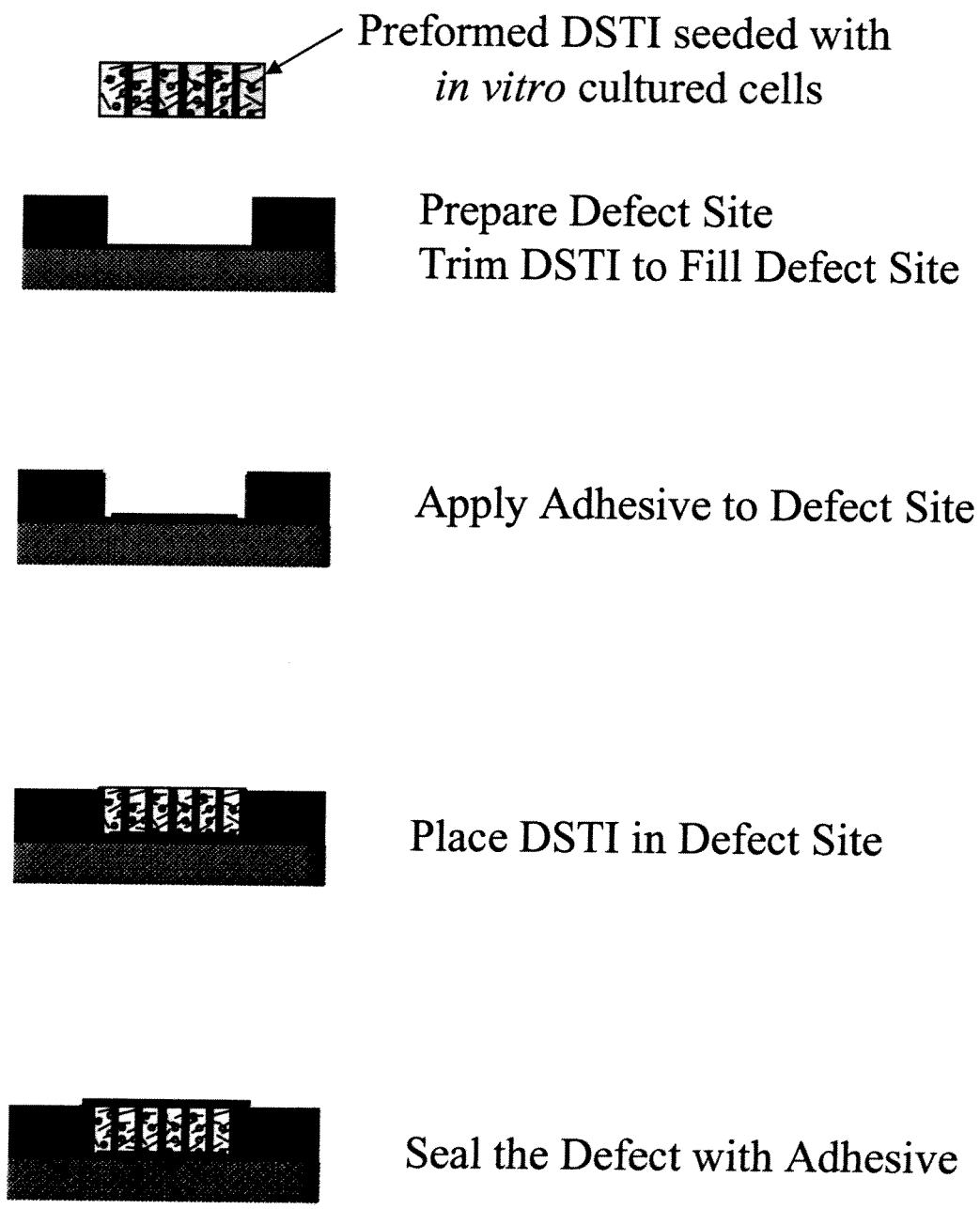
Figure 12F:
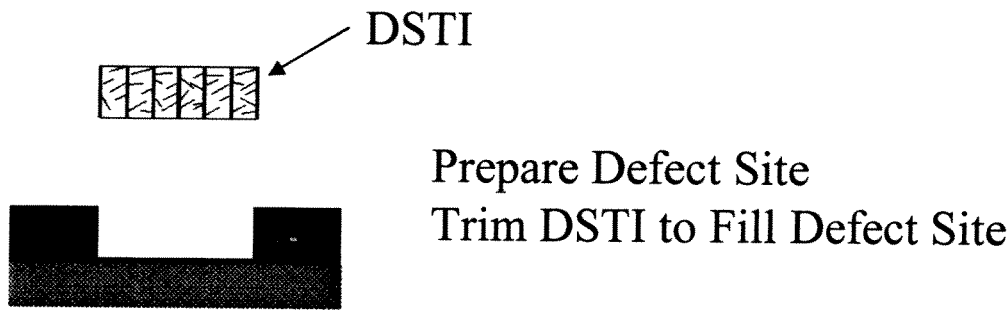
Figure 12F:
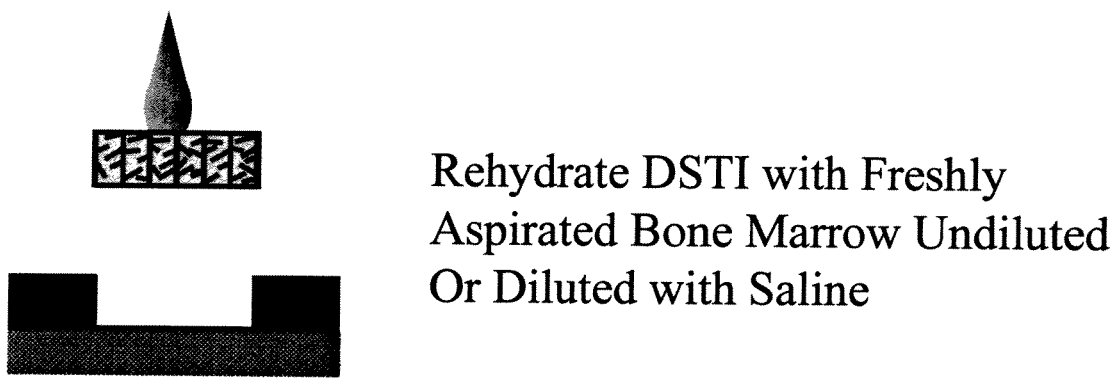
Figure 12F:
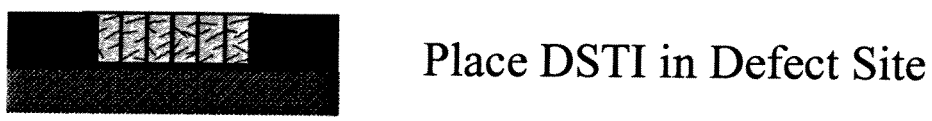
Figure 12F:
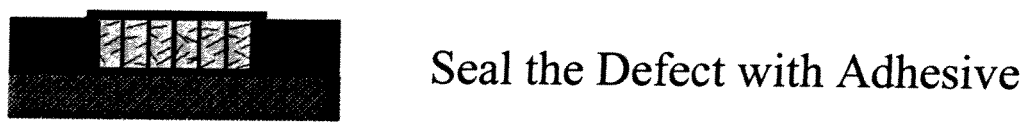

The rehydration time for each lot is less then 2 second evidencing a very fast wettability of the DSTI products.

viously trimmed DSTI to a size and shape of the defect. Rehydrated DSTI is implanted into the defect and sealed with an adhesive. FIG. 12B illustrates a method for implantation of the DSTI that is essentially the same as seen in FIG. 12A except that the subchondral plate is first penetrated with microfracture penetrations to permit migration of cells or marrow components from the underlying tissue into the DSTI implanted in the tissue lesion. In this method, the subchondral plate is penetrated and the rehydrated DSTI is placed in the defect as in FIG. 12A. After sealing the defect containing rehydrated DSTI with the adhesive, the marrow components are able to enter the DSTI through the microfracture. FIG. 12C illustrates a method for implantation of DSTI with microfracture as seen in FIG. 12B except that the adhesive previously applied only on the top of the DSTI and to seal the lesion is also applied to the bottom of the lesion in between the microfracture penetrations. Additionally, it can also be applied to the bottom of the lesion in instances when the migration of cells from the underlying tissue is undesirable. The FIG. 12D shows the implantation of the DSTI into the tissue lesion where the DSTI is rehydrated with mesenchymal stem cells (MSC). The DSTI rehydrated with MSC is then implanted into the tissue lesion and the defect is sealed with adhesive as described above. FIG. 12E show implantation of the DSTI seeded with bone marrow stem cells that were cultured in the DSTI prior its trimming into the size and shape of the lesion. In this instance the dry DSTI is rehydrated with the solution containing the MSC, cultured according to protocols used for such culturing in the presence of a culture medium optionally containing cell modulators. Such cell seeded DSTI could optionally be also activated by applying a hydrostatic/constant pressure regimen. The DSTI seeded with these cultured and/or activated cells is placed into the lesion or defect and the defect is sealed with adhesive placed over the implant. FIG. 12F illustrates implantation of the DSTI into the tissue defect where the DSTI is rehydrated with freshly aspirated bone marrow that is either undiluted or diluted with saline or another physiologically acceptable solution.

A. Use of DSTI for Treatment of Chondral Defects

One example of utility of the DSTI is its use for treatment of chondral defects.

To be successful for treatment of articular cartilage, the DSTI must provide conditions allowing the chondrocytes or mesenchymal stem cells seeded therein to be able to form and generate the new extracellular matrix. In this regard, the DSTI pore structure must allow cells to migrate into the pores and function similarly to their normal function in the healthy tissue. The extracellular matrix formed by the cells seeded within the DSTI then provides means for growing a new hyaline or hyaline-like cartilage for treatment, replacement or regeneration of the damaged or injured articular cartilage. Such treatment is currently difficult because of the unique properties of the articular cartilage that is not the same as and does not behave as other soft tissues.

As amply illustrated above, the DSTI of the invention provides all conditions necessary for migration or seeding the chondrocytes, stem cells, mesenchymal stem cells or bone marrow stem cells into the DSTI. Moreover, it provides conditions for their differentiation, transformation into chondrocytes, production of extracellular matrix as ultimately for production of a new hyaline cartilage. All these conditions may be enhanced with additions of cell mediators, using different culture conditions or by intermittently applying the hydrostatic pressure.

B. Use of DSTI for Treatment of Other Conditions

In addition to cartilage repair, a number of other acute or chronic conditions represent instances where the implantation of the double-structured tissue implant can provide a clinically important means for tissue repair.

The DSTI once placed at the site of tissue damage will provide a support for development of new tissues occurs in accordance with predefined configuration. For example, ischemic area in the myocardium may be treated with DSTI containing stem cells or mesenchymal stem cells differentiated into myocardial cells. In these applications, similarly to cartilage, the DSTI must resist, at least initially, the dynamic forces generated by the surrounding muscle and connective tissues and maintaining its structure during a necessary period of cellular infiltration, tissue formation and healing.

Since every tissue is a subject to metabolic turnover, the rapidity by which tissue differentiation and structural integrity are established is subject to various endogenous modulations, the ability to up-regulate or down-regulate such modulations through placement of specific signaling factors placed within the primary and secondary scaffold of the DSTI provides for vast therapeutic utility of the DSTI. Although the limits by which, for example, new muscle formation can be derived from progenitor cells suggests that localization of the mesenchymal cells to the site of damage in response to homing molecules, such as chemokines and cell receptor ligands, may be used to accelerate repair of muscle, either cardiac or skeletal, there must be a means to deliver these progenitor cells to such site. DSTI have been shown to be able to deliver these progenitor cells or modulators to the site of damage.

In another instance, wound healing applications have remained a primary goal in the use of tissue implants for cell-based tissue repair. Treatment of acute and chronic wounds is dependent on a multi-faceted transition by which progenitor cells encounter soluble mediators, form blood elements, extracellular matrix macromolecules and parenchymal cells that then serve to reestablish a body surface barrier through epithelization. In this instance either the double-structured tissue implant may provide a novice stromal layer into which blood vessels and progenitor cells can migrate. From this migration, the progenitor cells may then undergo differentiation into the fibroblast stromal cell and generate or recruit epithelial cells to support reestablishment of dermal and epidermal layers at the time of wound closure.

C. Basic Requirements for DSTI

The collagen-based primary and secondary scaffolds of the DSTI are essential components of the DSTI and are responsible for capability of DSTI to initiate the repair and induction of repair of tissue defects.

The first requirement is that the scaffolds are prepared from the biocompatible and preferably biodegradable materials that are the same or similar to those observed in the tissues to be repaired, hence the instant DSTI are prepared from collagen or collagen-like materials.

The second requirement is that the scaffolds have a spatial organization and orientation similar to that of the tissue to be repaired. The porous structure of both primary and secondary scaffold provides such organization.

The third requirement is that the scaffold have a pore density permitting the seeding or migration of the cells into said primary or secondary scaffolds in numbers needed for initiation of a tissue recovery or formation of new tissue in vivo. The substantially homogenous pore size and distribution within the DSTIs allows the cell seeding and assures cell viability.

The fourth requirement is that the scaffolds have a sufficient number of pores for the number of cells needed for initiation of the tissue recovery and repair. The spatial organization of both scaffolds have optimized number of pores and such number and pore size may be easily adjusted to the tissue requirement.

The fifth requirement is that the pores have substantially the same size and that such size is substantially the same from the top apical to the bottom basal surface of the pores, said pores being organized substantially vertically from the top to the bottom. The primary scaffold have such organization.

The sixth requirement is stability of the DSTI. The double-structured organization of the DSTI provides such stability during wetting, reconstitution, resistance to dissolution and to shrinkage or swelling.

The seventh requirement is that DSTI provides support and conditions for cell migration from the surrounding tissue, for integration of seeded cells into the surrounding tissue and generally that assures the cell viability. The DSTI provides such conditions and the cells seeded within DSTI have almost 100% viability.

V. Adhesives and Tissue Sealants

As described in the FIGS. 12A-12E, the double-structured tissue implant is implanted into a tissue defect or cartilage lesion covered with a biocompatible adhesive, tissue sealant or glue. Typically, the sealant is deposited over the implant after the implant is placed into the defect. However, in instances, such adhesive is also placed at the bottom of the lesion to prevent the migration of cells from the surrounding tissue or to prevent effects of endogenously present tissue modulators from interfering with a therapeutic effect of the DSTI. For example, when he DSTI is seeded with precultured cells or progenitor cells, a deposition of the adhesive to the bottom of the lesion is preferred. The adhesive is almost always used to cover the implanted DSTI.

Generally, the tissue sealant or adhesive useful for the purposes of this application has adhesive, or peel strengths at least 10 N/m and preferably 100 N/cm; has tensile strength in the range of 0.2 MPa to 3 MPa, but preferably 0.8 to 1.0 MPa. In so-called "lap shear" bonding tests, values of 0.5 up to 4-6 $N/cm^2$ are characteristic of strong biological adhesives.

Such properties can be achieved by a variety of materials, both natural and synthetic. Examples of suitable sealant include gelatin and di-aldehyde starch described in PCT WO 97/29715, 4-armed pentaerythritol tetra-thiol and polyethylene glycol diacrylate described in PCT WO 00/44808, photopolymerizable polyethylene glycol-co-poly(a-hydroxy acid) diacrylate macromers described in U.S. Pat. No. 5,410,016, periodate-oxidized gelatin described in U.S. Pat. No. 5,618,551, serum albumin and di-functional polyethylene glycol derivatized with maleimidyl, succinimidyl, phthalimidyl and related active groups described in PCT WO 96/03159.

Sealants and adhesives suitable for purposes of this invention include sealants prepared from gelatin and dialdehyde starch triggered by mixing aqueous solutions of gelatin and dialdehyde starch which spontaneously react and/or those made from a copolymer of polyethylene glycol and polylactide, polyglycolide, polyhydroxybutyrates or polymers of aromatic organic amino acids and sometimes further containing acrylate side chains, gelled by light, in the presence of some activating molecules.

Another type of the suitable sealant is 4-armed polyethylene glycol derivatized with succinimidyl ester and thiol plus methylated collagen in two-part polymer compositions that rapidly form a matrix where at least one of the compounds is polymeric, such as polyamino acid, polysaccharide, polyalkylene oxide or polyethylene glycol and two parts are linked through a covalent bond, for example a cross-linked derivatized PEG with methylated collagen, such as methylated collagen-polyethylene glycol.

Preferable sealants are 4-armed tetra-succinimidyl ester PEG, tetra-thiol derivatized PEG and PEG derivatized with methylated collagen, commercially available from Cohesion Inc., Palo Alto, Calif. and described in U.S. Pat. Nos. 6,312, 725B 1 and 6,624,245B2 and in *J. Biomed. Mater. Res.*, 58:545-555 (2001), *J. Biomed. Mater. Res.*, 58:308-312 (2001) and *The American Surgeon*, 68:553-562 (2002), all hereby incorporated by reference.

Sealants and adhesives described in copending U.S. application Ser. No. 10/921,389 filed Aug. 18, 2004 and Ser. No. 11/525,782 filed Dec. 22, 2006, are hereby incorporated by reference.

EXAMPLE 1

Preparation of the Primary Scaffold

This example describes one exemplary method for preparation of the collagen-based primary scaffold suitable as a structural support for preparation of the DSTI.

Type I collagen is dissolved in a weak hydrochloric acid solution at pH 3.0 with the collagen concentration and osmolality of the solution adjusted to about 3.5 mg/ml and 20 mOsm/kg, respectively. The solution (70 ml) is poured into a 100 ml Petri dish and the Petri dish containing the collagen solution is centrifuged at 400×g for 30 minutes to remove air bubbles. Neutralization and subsequent precipitation or gelling is carried out in a 7 liter chamber containing 10 ml of 15% ammonia solution over a 45 minutes period. The precipitated collagen is then washed in a large excess of de-ionized water. The water is changed as many times as needed over next 3 days to remove formed salts and excess ammonia.

The solution is then subjected to unidirectional freezing over a period of about 4 hours. The Petri dish is placed on a stainless steel disc which is partially submerged in a cooling bath. The temperature of the cooling bath is increased from 0° C. to −18° C. at a rate of 0.1° C./minute. The frozen water is removed by lyophilization over a period of about 3 days. The lyophilized primary scaffold is then dehydrothermally (DHT) treated at 135° C. for about 18 hours before being precut into slices of an appropriate thickness.

The organization of the newly synthesized cartilage specific matrix within the porous Type I collagen is visualized and quantified using histological and image analysis methods.

EXAMPLE 2

Preparation of a Basic Solution for a Secondary Scaffold

This example describes preparation of the Basic Solution used for formation of the secondary scaffold.

The Basic Solution comprises a soluble collagen in admixture with a PLURONIC® surfactant. The Basic Solution is incorporated into the primary scaffold and processes into the double scaffold tissue implant or processed as a stand alone implant.

Solution for the secondary scaffold is prepared by mixing PLURONIC® F127 (2.32 mg, 0.29 mg/ml), obtained commercially from BASF, Germany, with 8 ml of a solution containing 2.9 mg/ml bovine Type I collagen dissolved in hydrochloric acid (pH 2.0) at room temperature. The resulting solution is neutralized with 1 ml of 10× Dulbecco's phosphate buffered saline (DPBS) and 1 ml of 0.1M NaOH to the final pH of 7.4.

In the alternative, the neutralization is achieved by ammonia aqueous solution or ammonia vapor in concentration sufficient to neutralize acid within the collagen solution.

EXAMPLE 3

Preparation of the Double-Structured Tissue Implant

This example describes preparation of the double-structured tissue implant (DSTI). The preparation of DSTI includes incorporation of the Basic Solution for formation of a secondary scaffold within the primary scaffold and its further processing into DSTI.

4.9 ml (1.3×volume of the primary scaffold) of the neutralized basic collagen/PLURONIC® solution prepared in Example 2, is placed in a dish and a primary scaffold, prepared in Example 1, precut into a square having 50×50×1.5 mm dimensions is then placed into the neutralized Basic Solution for the secondary scaffold. The basic neutralized solution is absorbed into the primary scaffold by wicking or soaking.

The primary scaffold containing the neutralized solution is then placed in a 37° C. incubator over a period of 50 minutes to precipitate or gel the neutralized collagen solution. The composite consisting of the primary scaffold with the gelled or precipitated neutralized solution within is then washed in 500 ml of de-ionized water over a period of 30 minutes. The washed composite is placed on metal shelf of a freezer at a temperature −80° C. over a period of 30 minutes. The frozen composite is removed from the freezer and lyophilized.

Lyophilization is performed over a period of 18 hours. The lyophilized composite is then dehydrothermally treated at 135° C. under vacuum for a period of 6 hours to form the double-structured tissue implant (DSTI).

The DSTI is removed from the dehydrothermal oven and transferred aseptically into a Bio Safety Cabinet (BSC) where it is packaged.

EXAMPLE 4

Testing of Viability, Growth and Functionality of Cell seeded into DSTI

This example describes procedure used for determination of viability, growth and functionality of cells seeded into the DSTI.

Human chondrocytes obtained from NDRI Research Services depository were dissolved in 30 μl of culture medium and the medium containing the chondrocytes was placed into culture plates and the 6 mm DSTI discs were placed into the culture medium containing the cells. The cells were allowed to penetrate the discs for about 1 hour at which time 1 ml of medium was added to the wells. For comparison, human chondrocytes were introduced into 6 mm discs of a well-characterized non-lyophilized 3-dimensional honeycomb collagen scaffold. The discs were incubated for 1 or 21 days at 2% $O_2$ and 37° C. % $CO_2$. Medium was changed twice weekly. On termination 3 discs were taken for viability testing and 3 for GAG and DNA analysis.

EXAMPLE 5

Testing Viability of Cell Cultured in the DSTI

This example describes a procedure used for testing of cell viability.

Three DSTI discs (DSTI-1, DSTI-2 and DSTI-3) obtained in Example 4 were used for viability testing. Each DSTI was digested with collagenase at 37° C. for 1 hour and the digest was centrifuged to obtain a cell pellet. The pellet was dispersed into an aliquot of culture medium and a cell count was performed using trypan blue exclusion test to determine the total number of cells and the percent of live cells that were retained in the DSTI. over the course of 21 days in culture.

Results were described above in Table 1. All three discs have shown at least 97% viability initially and such viability increased after 3 weeks in culture.

EXAMPLE 6

S-GAG and DNA Assays

This example describes procedure used for determination of S-GAG and DNA.

The DSTI discs obtained in Example 4 were digested with papain at 56° C. overnight. An aliquot of the digest was taken for analysis of S-GAG content by the DMMB assay and an additional aliquot was used to measure DNA by Hoechst dye.

EXAMPLE 7

Determination of Cell Attachment Growth and Differentiation

This example describes conditions for determination of the ability of multipotent, undifferentiated bone marrow stem cells to attach, grow and differentiate into chondrocytes in DSTI.

Human bone marrow mesenchymal stem cells (HBMSC) were purchased from Lonza and maintained in culture with bone marrow stem cells growth media containing 10% FBS. Human articular chondrocytes (hAC) were extracted by placing finely minced cartilage in a collagenase solution overnight. Liberated cells were then plated on tissue culture plastic in chondrocyte growth media (DMEM/F12+10% FBS). At confluence, BMSC and hAC were lifted with 0.05% Trypsin+ 0.01% EDTA and cells were counted. The DSTI was cut into discs (6×1 mm diameter) using a biopsy punch, placed on Teflon® dishes and seeded by aliquoting 95,000 cells in 30 μl growth media on top of each DSTI. The cells were allowed to attach for 1 hour. Seeded DSTIs were then placed in individual 15 ml polypropylene tubes and incubated with either 0.5 ml growth media or complete chondrogenic medium (Lonza, serum-free+TGFβ3), and placed in 37° C. incubators at 2% $O_2$, Medium was replaced twice weekly. At 2 and 4 weeks, individual DSTIs were removed and analyzed for DNA content using the Hoechst assay; S-GAG using dimethylene blue assay. RT-PCR was used for RNA expression of Type I collagen (COL1AI), Type II collagen (COL2A 1), and aggrecan (AGC1) measurements. The measurements were corrected using 188 and β-actin (ACTβ). All primers were obtained from Applied Biosystems.

EXAMPLE 8

Boyden Chamber Assay

This example describes conditions used for determination of migration of cells into DSTI using a Boyden chamber assay.

A Boyden chamber was placed in a 24 well plate and 50,000 cells of undifferentiated bone marrow stem cells or human articular chondrocytes were plated on the 8 μm pore size membrane and allowed to attach for 48 hours in 200 μl growth medium. A DSTI disc (6 mm diameter) was then placed in the bottom portion of the chamber and 600 μl growth or chondrogenic induction medium was placed in the lower chamber and incubated at low $O_2$. Media was replaced 2 times per week. Cells begin to migrate into the lower chamber and into DSTI, and differentiate into chondrocytes. Following 1, 2, or 3 weeks, DSTI were analyzed for biochemical determination of S-GAG, DNA, and for gene expression by RT-PCR.

Certain modifications to a classical Boyden chamber assay were introduced. Membrane inserts with 8 μm pore size were placed in individual wells of a 24 well plate. 50,000 human articular chondrocytes or bone marrow stem cells were plated in the top chamber in growth media and allowed to attach for 48 hours with nothing in the bottom chamber. This allowed cells to attach and form a barrier that leads to decreased permeability to the lower chamber, allowing a unidirectional effect from top to bottom chambers. Following 1, 2, and 3 weeks in culture, DSTI were assayed by DNA/GAG, and RT-PCR.

EXAMPLE 9

Determination of DSTI Chemoattractant Potential

This example describes procedure used for determination of chemoattractant potential of the DSTI.

Approximately 50,000 cells/insert were seeded onto the top chambers of 8 μm pore Boyden Chambers and filled with DMEM/12 medium supplemented with 1% bovine serum albumin (BSA). The lower chambers contained 6 mm DSTIs or were left empty and were filled with one of three medium formulations: the same medium as in the top chamber (1% BSA medium), growth medium (DMEM/F12 medium supplemented with 10% fetal bovine serum (FBS)) or chondrogenic medium (Lonza medium supplemented with TGFβ3).

The movement of cells through the membrane was observed at 4 hours and at 18 hours. Medium was aspirated from the upper chamber and the membrane swabbed to remove cells still on top. The membrane was then fixed with methanol and stained by immunofluorescence with actin and DAPI to visualize and count the cells that penetrated the membrane. Six high power fields were counted using a fluorescence microscope and the mean±standard deviation was calculated for each group at each time point.

EXAMPLE 10

Method of Improvement of Differentiation

This example describes a protocol used for determination of cell differentiation.

Approximately 50,000 MSC per one Boyden Chamber were seeded onto the top chambers of 8 μm pore Boyden chambers and filled with Advanced Dulbecco's Minimal Essential Medium (ADMEM) medium supplemented with 1% BSA. The lower chambers were either empty or contained DSTI or DSTI loaded with 250 ng RGMA in 30 μl PBS and allowed to absorb into the scaffold for 60 minutes prior to start of experiment. 500 μl ADMEM containing 10% FBS was placed in the lower chamber. After 18 hours, medium was aspirated from the upper chamber and the membrane swabbed to remove cells on top. The membranes were then fixed with methanol and stained by immunofluorescence with 4,6-diamino-6-phenylindole (DAPI) to visualize and count the cells that penetrated the membrane. Six high power fields were counted using a fluorescence microscope and the mean±standard deviation was calculated for each group at each time point.

EXAMPLE 11

Assay for Determination of Differentiation of Mesenchymal Stem Cells

This example describes procedure used for determination of fo differentiation of mesenchymal stem cells.

Human bone marrow mesenchymal stem cells (MSC) were purchased from Lonza and maintained in culture with bone marrow stem cells growth media containing 10% FBS. Human articular chondrocytes (hAC) were extracted by placing finely minced cartilage in a collagenase solution overnight. Liberated cells were then plated on tissue culture plastic in chondrocyte growth media (DMEM/F12+10% FBS). At confluence, MSC and hAC were lifted with 0.05% Trypsin+ 0.01% EDTA and cells were counted. A Boyden Chamber of 8 μm pore size was placed in a 24 well plate and 50,000 cells of undifferentiated MSC or hAC were plated on the insert and allowed to attach for 72 hours in 200 μl growth medium. A DSTI disc (6 mm diameter×10.5 m thickness) was then placed in a 24 chamber and hydrated with 30 μl PBS (control) or 100 ng BMP-2, 100 ng BMP-7, or 250 ng RGMA and allowed to absorb into the DSTI for 1 hour. 500 μl of growth medium was placed in the lower chamber together with DSTI preloaded with drug. Medium in the upper chamber was replaced with 200 μl DMEM/F12+1% BSA and the DSTI is placed into the medium. Cells were allowed to migrate, proliferate, and differentiate for 72 hours. Following 72 hours, DSTI in the lower chamber was placed in TRIzol to extract RNA. In the longer 3 weeks experiments, DSTI were either placed in TRIzol to extract RNA for RT-PCR or placed in buffered formalin for histological analyses

EXAMPLE 12

Method for Production of Hyaline Cartilage

This example describes a protocol for investigation of production of hyaline cartilage using cultured seeded mesenchymal stem cells and human articular chondrocytes.

Human bone marrow mesenchymal stem cells (MSC) were purchased from Lonza and maintained in culture with bone marrow stem cells growth media containing 10% FBS. Human articular chondrocytes (hAC) were extracted by placing finely minced cartilage in a collagenase solution overnight. Liberated cells were then plated on tissue culture plastic in chondrocyte growth media (DMEM/F12+10% FBS). At confluence, MSC and hAC were lifted with 0.05% Trypsin+ 0.01% EDTA and cells were counted. A Boyden chamber of 8 μm pore size was placed in a 24 well plate and 50,000 cells of undifferentiated MSC or hAC were plated on the insert and allowed to attach for 72 hours in 200 μl growth medium. A DSTI disc (6 mm diameter×10.5 m thickness) was placed in a 24 well plate and hydrated with 30 μl PBS (control) or 100 ng BMP-2, 100 ng BMP-7, or 250 ng RGMA and allowed to absorb into the DSTI for 1 hour. 500 μl of growth medium was placed in the lower well with the drug preloaded DSTI. Medium in the upper insert was replaced with 200 μl DMEM/ F12+1% BSA and the DSTI was placed in the chamber. Cells are allowed to migrate, proliferate, and differentiate for 3 weeks. Medium is replaced twice weekly; in half of the growth factor conditions, fresh growth factor is added to the lower well in the same concentrations as above. After 3 weeks, DSTI was placed in TRIzol to extract RNA for RT-PCR analyses.

EXAMPLE 13

The Effect of Hydrostatic Pressure on Cell Differentiation in DSTI

This example describes a protocol used for determination of the effect of hydrostatic pressure on cell differentiation using DSTI.

Bone marrow stem cells or human articular chondrocytes were seeded into DSTI and placed in growth medium or chondrogenic medium. The human articular chondrocytes or bone marrow stem cells were seeded onto DSTI and allowed to attach for 48 hours. DSTIs were then either placed in static conditions for 21 days or were subjected to TEP for 7 days followed by static for 14 days. In both situations, chondrogenic media was used for the first 7 days followed by 3D media (DMEM:F12 supplemented with 10% FBS and ITS) for the following 14 days. DSTIs were analyzed for histology by Safranin-O, for biochemical determination of S-GAG by DMB, DNA by Hoechst dye assay, and gene expression by RT-PCR.

EXAMPLE 14

Determination of Retention of Collagen within DSTI

This example describes a procedure used for determination of the stability of the double-structured tissue implant in vitro.

Three lots of DSTIs are prepared as described in Example 4 and cut to a size of 1.5×1.5×0.15 cm. Cut DSTIs are placed in 35 mm Petri dishes, rehydrated with 450 m of phosphate buffered saline and additional 2 ml of phosphate buffered saline are added to each Petri dish containing the DSTI. The analysis for each lot consist of three replicates for a total of 9 samples for the three lots.

Dishes containing individual DSTIs are placed in the incubator for the duration of testing. In the predetermined intervals of zero hour, 1 hour, 3 days, 7 days and 14 days, 1 ml aliquot of the phosphate buffered saline is removed from each plate. Each removed 1 ml is replaced with 1 ml of a fresh phosphate buffer saline. The removed aliquots are subjected to a calorimetric protein assay for quantification of total collagen released into the saline.

Cumulative collagen retention curves are generated by subtraction of the amount of collagen released into the solution from the theoretical collagen load estimated at 0.777 mg of collagen/DSTI sample.

What is claimed:

1. An implant for repairing a cartilage or a tissue defect comprising:
    an acellular, three-dimensional scaffold comprising collagen and defining a plurality of pores;
    a lyophilized and dehydrothermally-treated composition having a basic pH and comprising a collagenous solution or gel and a surfactant, wherein the composition fills the plurality of pores and forms a fibrous and cross-linked collagen network within the plurality of pores; and
    a plurality of cells selected from the group consisting of chondrocytes, stromal cells, stem cells, and bone marrow aspirate, seeded within the implant.

2. The implant of claim 1, wherein the acellular, three-dimensional scaffold is a biodegradable sponge, a honeycomb or honeycomb-like scaffold, or a thermo-reversible hydrogel (TRGH).

3. The implant of claim 1, wherein the acellular, three-dimensional scaffold is prepared from a compound selected from the group consisting of Type I collagen, Type II collagen, Type III collagen, Type IV collagen, and Type V collagen.

4. The implant of claim 1, wherein the plurality of pores are substantially uniform in size with a defined diameter of about 300±100 μm, and wherein the sizes and diameters of the pores on both a top surface and a bottom surface are substantially the same.

5. The implant of claim 4, wherein the plurality of pores are vertically oriented.

6. The implant of claim 4, further comprising a morphogenetic growth factor incorporated therein.

7. The implant of claim 4, wherein the plurality of cells comprise stem cells.

8. The implant of claim 4, further comprising a morphogenetic growth factor incorporated therein.

9. The implant of claim 1, wherein the collagenous solution or gel comprises Type 1 collagen, Type II collagen, methylated collagen, gelatin, or any combination thereof.

10. The implant of claim 1, wherein the surfactant is ionic or non-ionic.

11. The implant of claim 10, wherein the surfactant is a derivatized polyethylene glycol or a block co-polymer of polyoxyethylene (PEO) and polyoxypropylene (PPO) having the generic organization of polymeric blocks PEG-PPO-PEG or PPO-PEG-PPO.

12. The implant of claim 11, wherein the derivatized polyethylene glycol is polyethylene glycol p-(1,1,3,3-tetramethylbutyl)-phenyl ether.

13. The implant of claim 11, wherein the block co-polymer is a polymer of polyoxyethylene (PEO) and polyoxypropylene (PPO) with two 96-unit hydrophilic PEO chains surrounding one 69-unit hydrophobic PPO chain.

14. The implant of claim 1, wherein the plurality of cells comprise human articular chondrocytes.

15. The implant of claim 1, wherein the plurality of cells comprise mesenchymal stem cells, neural stem cells, or bone marrow stem cells.

16. The implant of claim 1, wherein the tissue defect comprises tissue selected from a group consisting of chondral, muscle, vascular, cardiac, epithelial, or neural tissue.

17. The implant of claim 1, further comprising a cell modulator incorporated therein.

18. The implant of claim 17, wherein the cell modulator is selected from a group consisting of a pharmaceutical agent, a growth factor, a growth hormone, a mediator, an enzyme promoting cell incorporation, an enzyme promoting cell proliferation, an enzyme promoting cell division, a pharmaceutically acceptable excipient, an additive, and a buffer.

19. The implant of claim 18, wherein the growth factor comprises a transforming growth factor, an insulin-like growth factor 1, a platelet-derived growth factor, a repulsive guidance molecule or a bone morphogenetic protein (BMP).

20. The implant of claim 1, wherein the dehydrothermally-treated composition was subjected to a temperature between about 70° C. to about 200° C., for about 30 minutes to about 7 days, under a vacuum.

* * * * *